(12) United States Patent
Onyuksel et al.

(10) Patent No.: US 9,561,286 B2
(45) Date of Patent: Feb. 7, 2017

(54) STERICALLY STABILIZED CATIONIC NANOCARRIER, KITS AND METHOD OF USE

(71) Applicant: The Board of Trustees of the University of Illinois, Urbana, IL (US)

(72) Inventors: Hayat Onyuksel, Western Springs, IL (US); Fatima A. Khaja, Bloomingdale, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 15/060,663

(22) Filed: Mar. 4, 2016

(65) Prior Publication Data

US 2016/0256559 A1 Sep. 8, 2016

Related U.S. Application Data

(60) Provisional application No. 62/129,066, filed on Mar. 6, 2015.

(51) Int. Cl.
*A61K 9/127* (2006.01)
*A61K 48/00* (2006.01)
*A61K 47/48* (2006.01)
*C12N 15/113* (2010.01)

(52) U.S. Cl.
CPC ... *A61K 47/48215* (2013.01); *A61K 47/48053* (2013.01); *A61K 47/48338* (2013.01); *C12N 15/113* (2013.01); *C12N 2310/14* (2013.01)

(58) Field of Classification Search
None
See application file for complete search history.

(56) References Cited

U.S. PATENT DOCUMENTS

2015/0297749 A1* 10/2015 Hahn ................. A61K 49/1839
424/1.37

OTHER PUBLICATIONS

Zheng et al (Blood 113(12):2646-2654, 2009).*
Kale et al (Journal of Drug Targeting, Aug.-Sep. 2007; 15(7-8): 538-545).*
Akinc et al. "Exploring polyethylenimine-mediated DNA transfection and the proton sponge hypothesis" J. Gene Med. 2005 7(5):657-663.
Ameyar-Zazoua et al. "siRNA as a route to new cancer therapies" Exp. Opin. Biol. Ther. 2005 5(2):221-4.
Davis "The first targeted delivery of siRNA in humans via a self-assembling, cyclodextrin polymer-based nanoparticle: from concept to clinic" Mol. Pharm. Mol. Pharmaceut. 2009 6(3):659-668.
Hernandez-Gea & Friedman "Pathogenesis of liver fibrosis" Ann. Rev. Pathol. 2011 6:425-56.
Khaja et al. "A Novel Targeted siRNA Nanomedicine: Galactosamine Conjugated Sterically Stabilized Phospholipid Nanoparticles for siRNA Delivery" AAPS J. 2012 14(S2).
Luo et al. "Inhibition of connective tissue growth factor by small interfering RNA prevents renal fibrosis in rats undergoing chronic allograft nephropathy" Transplant Proc. 2008 40(7):2365-9.
Marrink et al. "Simulation of the spontaneous aggregation of phospholipids into bilayers" J. Am. Chem. Soc. 2001 123(35):8638-8639.
Pecot et al. "RNA interference in the clinic: challenges and future directions" Nat. Rev. Cancer 2011 11(1):59-67.
Semple et al. "Rational design of cationic lipids for siRNA delivery" Nat. Biotechnol. 2010 28(2):172-6.
Timko et al. Advances in Drug Delivery Annu. Rev. Mater. Res. 2011 41(1):1-20.
Whitehead, et al. "Knocking down barriers: advances in siRNA delivery" Nat. Rev. Drug Discov. 2009 8(2):129-138.
Gao et al. "Research progress on siRNA delivery with nonviral carriers" Int. J. Nanomed. 2011 6:1017-25.
Gavrilov & Saltzman "Therapeutic siRNA: principles, challenges, and strategies" Yale J. Biol. Med. 2012 85(2):187-200.
George & Tsutsumi "siRNA-mediated knockdown of connective tissue growth factor prevents N-nitrosodimethylamine-induced hepatic fibrosis in rats" Gene Ther. 2007 14(10):790-803.
Gressner & Gressner "Connective tissue growth factor: a fibrogenic master switch in fibrotic liver diseases" Liver Int. 2008 28(8):1065-1079.
Khaja et al. "A Novel Targeted siRNA Nanomedicine: Galactosamine Conjugated Sterically Stabilized Phospholipid Nanoparticles for siRNA Delivery" CRS Annual Meeting Abstracts 2013 714.
Ozpolat, et al. "Nanomedicine based approaches for the delivery of siRNA in cancer" J. Intern. Med. 2010 267(1):44-53.
Phanish, et al. "Connective tissue growth factor-(CTGF, CCN2)—a marker, mediator and therapeutic target for renal fibrosis" Nephron Exp. Nephrol. 2010 114(3):e83-92.
Schroeder et al. "Lipid-based nanotherapeutics for siRNA delivery" J. Intern. Med. 2010 267(1):9-21.
Shi et al. "Biodistribution of small interfering RNA at the organ and cellular levels after lipid nanoparticle-mediated delivery" J. Histochem. Cytochem. 2011 59(8):727-740.
Whitehead, et al. "Synergistic silencing: combinations of lipid-like materials for efficacious siRNA delivery" Mol. Ther. 2011 19(9):1688-94.
Yu et al. "Lipid nanoparticles for hepatic delivery of small interfering RNA" Biomaterials 2012 33(25):5924-5934.
Zuhorn et al. "Gene delivery by cationic lipid vectors: overcoming cellular barriers" Eur. Biophys. J. 2007 36(4-5):4-5.

* cited by examiner

*Primary Examiner* — Richard Schnizer
(74) *Attorney, Agent, or Firm* — Licata & Tyrrell P.C.

(57) ABSTRACT

A compound composed of a phospholipid and basic amino acid residues is provided as is a sterically stabilized phospholipid nanocarrier containing the compound and use of the same in passive and targeted delivery of negatively charged therapeutic agents encapsulated within the nanocarrier.

25 Claims, 4 Drawing Sheets

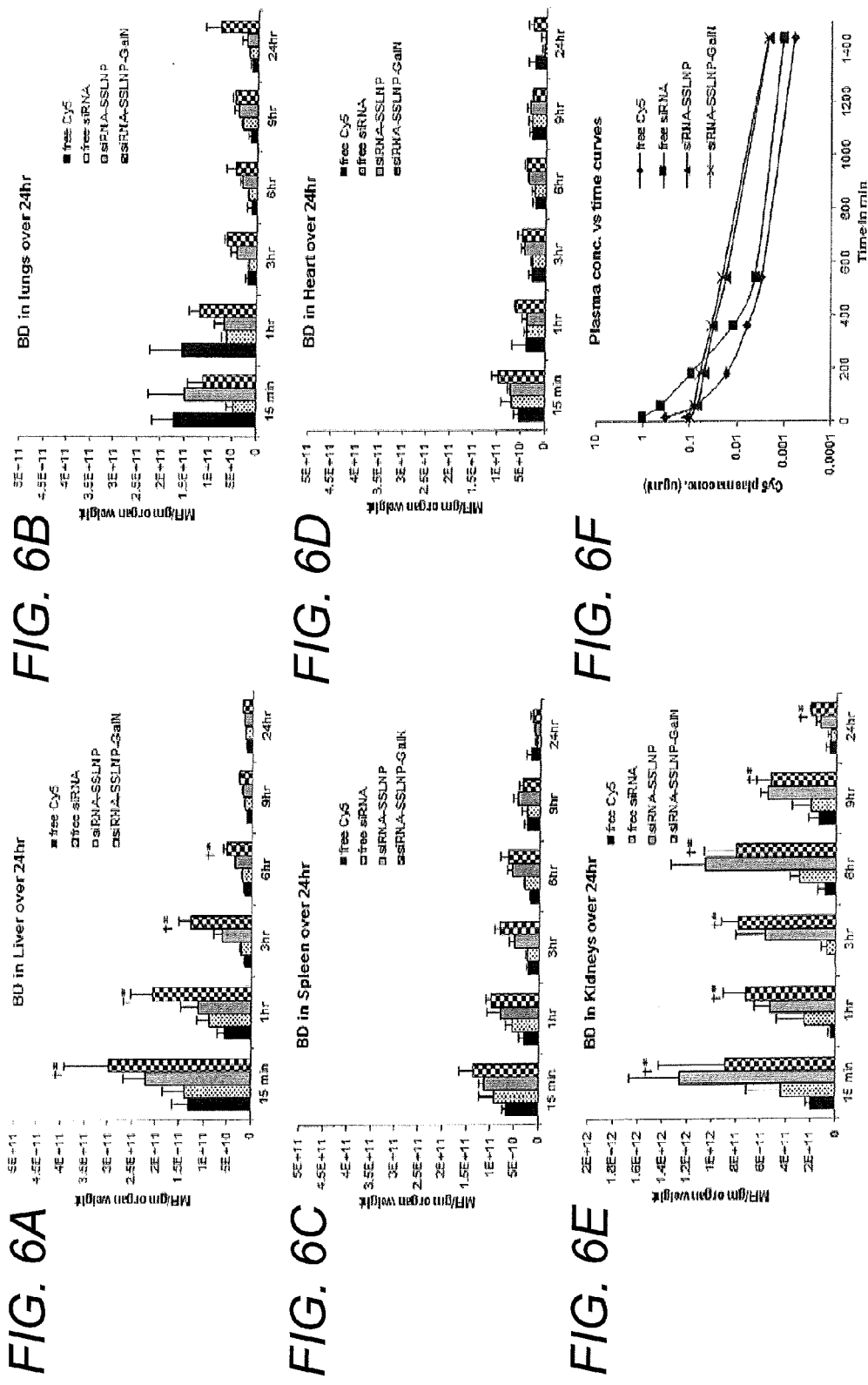

STERICALLY STABILIZED CATIONIC NANOCARRIER, KITS AND METHOD OF USE

INTRODUCTION

This application claims benefit of priority to U.S. Provisional Application Ser. No. 62/129,066 filed Mar. 6, 2015, the contents of which is herein incorporated by reference in its entirety.

BACKGROUND

Small interfering RNA (siRNA) has been considered as a potent tool for modulating gene expression because of its high specificity to target proteins that are not easily accessed by conventional small molecules (Gavrilov & Saltzman (2012) *Yale J. Biol. Med.* 85(2):187-200), hence RNAi therapeutics have demonstrated great therapeutic potential in the treatment of many devastating diseases such as cancer (Ozpolat, et al. (2010) *J. Intern. Med.* 267(1):44-53; Ameyar-Zazoua, et al. (2005) *Exp. Opin. Biol. Ther.* 5(2):221-4). However, as a naked molecule, siRNA is small and highly charged, making it susceptible to degradation, clearance and wide biodistribution (Whitehead, et al. (2011) *Mol. Ther.* 19(9):1688-94; Timko, et al. (2011) *Annu. Rev. Mater. Res.* 41(1):1-20; Shi, et al. (2011) *J. Histochem. Cytochem.* 59(8):727-740). On the other hand, developing carrier systems that can protect and target it to its intended site of action has shown other production and safety challenges (Whitehead, et al. (2009) *Nat. Rev. Drug Discov.* 8(2):129-138; Zuhorn, et al. (2007) *Eur. Biophys. J.* 36(4-5):4-5). These reasons collectively have limited siRNA applications beyond preclinical studies making RNAi therapeutics an unmet medical need.

Synthetic cationic materials have demonstrated considerable potential as nonviral siRNA delivery vehicles (Zuhorn, et al. (2007) supra; Yu, et al. (2012) *Biomaterials* 33(25): 5924-5934). Cationic materials offer several benefits, including the ability to facilitate cellular uptake through contact with the negatively charged cellular membrane, enables complex formation by compressing the negatively charged siRNA through electrostatic interactions, and can potentially assist in proton sponge-mediated endosomal escape as they become more protonated with pH drop (Akinc, et al. (2005) *J. Gene Med.* 7(5):657-663). Yet use of these materials (e.g., polymers and cyclodextrins) has not progressed beyond initial clinical studies (Davis (2009) *Mol. Pharm. Mol. Pharmaceut.* 6(3):659-668) as they pose complexity, toxicity and expense barriers (Gao, et al. (2011) *Int. J. Nanomed.* 6:1017-25; Schroeder, et al. (2010) *J. Intern. Med.* 267(1):9-21). Therefore, developing an efficient inexpensive and safe delivery system is the greatest challenge associated with moving RNAi therapeutics from the bench to the bedside.

Lipid nanoparticles in general and phospholipids in particular have been generally recognized as one of the most promising delivery systems for siRNA due to their biocompatibility and ease of large scale production as well as their recent utilization in clinical trials (Yu, et al. (2012) supra; Pecot, et al. (2011) *Nat. Rev. Cancer* 11(1):59-67). Phospholipids are amphiphilic molecules that display physicochemical properties of naturally occurring lipids, forming a spontaneous bilayer structure upon dispersion in water (Marrink, et al. (2001) *J. Am. Chem. Soc.* 123(35):8638-8639), entrapping the dispersed payload within the core of the formed structure (Semple, et al. (2010) *Nat. Biotechnol.* 28(2):172-6; Schroeder, et al. (2010) *J. Intern. Med.* 267(1): 9-21).

Connective tissue growth factor (CTGF) is considered the master switch in chronic fibrotic diseases (Phanish, et al. (2010) *Nephron Exp. Nephrol.* 114(3):e83-92; Gressner & Gressner (2008) *Liver Int.* 28(8):1065-1079), and provides a unique strategy for siRNA targeted therapeutics. Following chronic organ injury, CTGF is overexpressed, as a part of the wound healing response, exerting its own profibrotic effect as well as facilitating the profibrotic effect of transforming growth factor (TGF-β1). Both work synergistically causing activation of endothelial cells into proliferative myofibroblasts, causing the accumulation of collagen and other proteins in the surrounding extracellular matrix (ECM) and affecting the organ morphology and function (Phanish, et al. (2010) supra; Hernandez-Gea & Friedman (2011) *Ann. Rev. Pathol.* 6:425-56). Down-regulation of CTGF expression has been shown to be an effective strategy for the reversal of endothelial cells activation and accumulation of fibrotic ECM (Luo, et al. (2008) *Transplant Proc.* 40(7):2365-9; George & Tsutsumi (2007) *Gene Ther.* 14(10):790-803). The use of siRNA nanomedicine to target CTGF has been suggested (Khaja, et al. (2012) *AAPS J.* 14(S2); Khaja, et al. (2013) *CRS Annual Meeting Abstracts* 714).

SUMMARY OF THE INVENTION

The present invention is a sterically stabilized nanocarrier containing a PEGylated phospholipid complexed with one or more cationic phospholipids, wherein said sterically stabilized nanocarrier has a particle size of about 10 nm to about 100 nm. In some embodiments, the PEGylated phospholipid is distearoylglycerophosphoethanolamine-PEG$_{2000}$ and the cationic phospholipid has the structure of Formula I, Formula II or Compound 1. In other embodiments, the nanocarrier further includes a targeting ligand and/or a therapeutic agent, e.g., an RNAi, antisense, or ribozyme molecule. Methods for delivering a therapeutic agent to a subject and preventing or treating a disease or condition (e.g., renal fibrosis, liver fibrosis or cirrhosis) with a sterically stabilized nanocarrier of this invention are also provided.

The invention also provides a compound of Formula I:

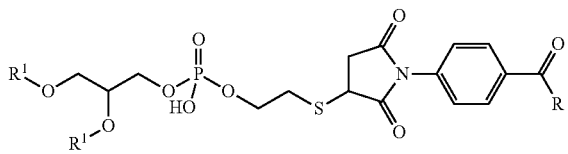

Formula I wherein R is a linear chain of between 1 and 10 basic amino acid residues and each R$^1$ is independently a saturated or unsaturated acyl chain of between 16 and 18 carbon atoms. In some embodiments, the compound has the structure of Formula II, or more particularly, Compound 1. A sterically stabilized nanocarrier containing the compound is also provided, wherein said nanocarrier optionally includes a PEGylated phospholipid, a targeting ligand and/or a therapeutic agent, e.g., RNAi, antisense, or ribozyme molecule. A kit containing the compound and a PEGylated phospholipid is also encompassed by this invention.

BRIEF DESCRIPTION OF THE DRAWINGS

FIG. 3A, changes in FACS histogram indicative of siRNA positive cells. FIG. 3B, bars represent quantitative analysis of FACS histogram as a percentage siRNA-positive cells. *$p<0.05$ vs free siRNA and untreated control, † $p>0.05$ vs siRNA-LF treated cells. FIG. 3C, relative Hep-G2 cell viability expressed as a percentage of untreated control as a measure of cytotoxicity of siRNA complexes using MTS assay.

FIGS. 6A-6F shows the biodistribution of different siRNA formulations compared to free Cy5 fluorophor over a 24-hour period in liver (FIG. 6A), lung (FIG. 6B), spleen (FIG. 6C), heart (FIG. 6D) and kidneys (FIG. 6E). Targeted formulation (siRNA-SSLNP-GalN) shows significant accumulation in liver and kidneys over observation period. n=4 for each time point, *$p<0.05$ vs free siRNA treated animals, † $p<0.05$ vs free Cy5 treated animals. FIG. 6F shows plasma concentration vs time curves of various formulations presented as two-compartmental model and used to calculate PK parameters.

DETAILED DESCRIPTION OF THE INVENTION

Figure 1:
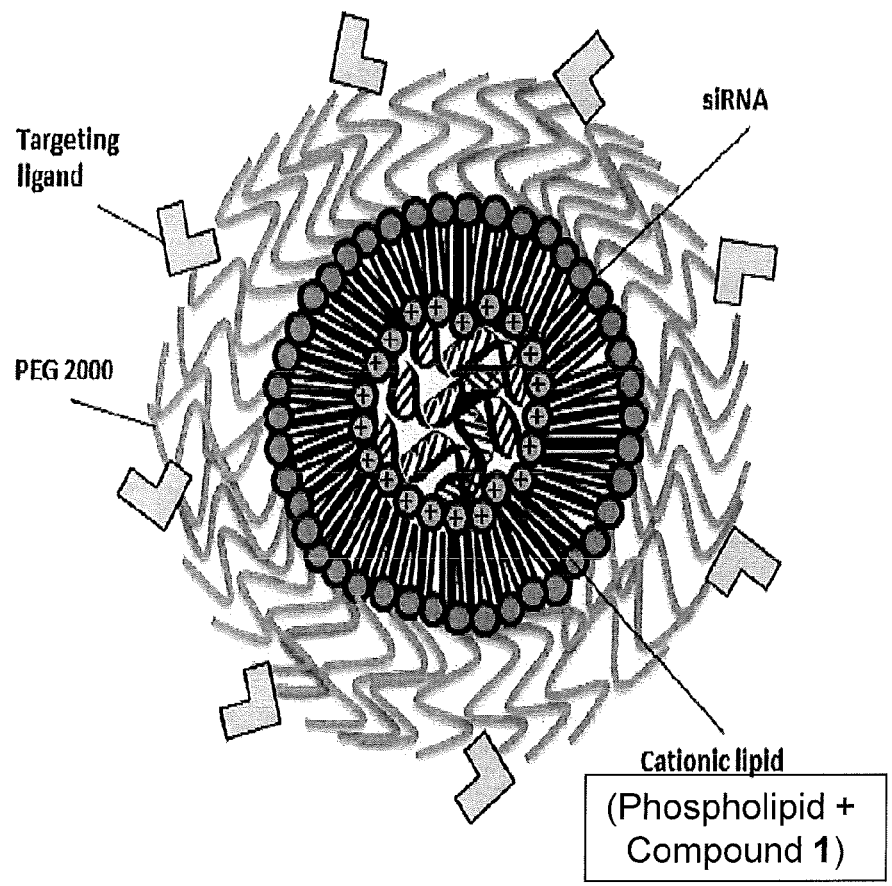
FIG. 1 depicts that structure of the Sterically Stabilized Phospholipid siRNA Nanocarrier (SSLNP) of the present invention.

RNAi therapeutics represents an emerging modality for the treatment of many devastating diseases. Because of siRNA low serum stability, the development of a safe and effective in vivo delivery system is of importance to realize the effectiveness of RNAi therapeutics. A sterically stabilized phospholipid nanocarrier (FIG. 1) has now been developed, characterized and evaluated for the passive and targeted delivery of siRNA in vitro and in vivo. The nanocarrier of this invention includes a PEGylated phospholipid and a novel molecule composed of a cationic phospholipid, wherein the phosphate group of the phospholipid is conjugated to a linear chain of between 1 and 10 basic amino acid residues. Upon conjugation to a targeting ligand, the nanocarrier was shown to efficiently delivery siRNA into cells with significantly lower cytotoxicity than LIPOFECTAMINE, facilitate gene silencing and enhance retention in targeted cells.

Accordingly, this invention provides a cationic phospholipid, a sterically stabilized nanocarrier containing said cationic phospholipid and methods for using the sterically stabilized nanocarrier for delivering therapeutic agents, in particular iRNA therapeutics, in the prevention and/or treatment of diseases or conditions. As used herein, the cationic phospholipid of the invention is composed of two saturated or unsaturated acyl chain groups (i.e., fatty acid tails), wherein the phosphate group of the phospholipid is conjugated via a bifunctional crosslinker to a linear chain of between 1 and 10 basic amino acid residues, i.e., a peptide. In some embodiments, the acyl chains of the phospholipid are selected from palmitoyl, oleoyl, stearoyl or a mixture of any two acyl chains with different lengths, e.g., between 16 and 18 carbon atoms. In another embodiment, the basic amino acid residues of the cationic phospholipid are arginine, lysine, or histidine, or a combination thereof. In a further embodiment, the heterobifunctional crosslinker contains N-hydroxysuccinimide (NHS) ester and maleimide groups.

In certain embodiments of the invention, the cationic phospholipid has the structure of Formula I,

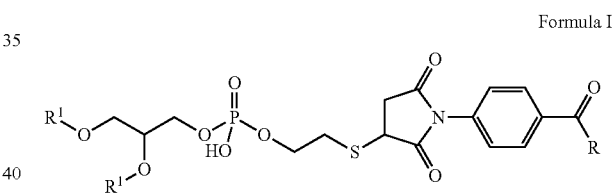

Formula I wherein R is a linear chain of between 1 and 10 basic amino acid residues and each $R^1$ is independently a saturated or unsaturated acyl chain of between 16 and 18 carbon atoms. In some embodiments, the linear chain of basic amino acid residues is composed of arginine, lysine, or histidine or a combination thereof. In other embodiments, the linear chain of basic amino acid residues is a peptide of 2, 3, 4, 5, 6, 7, 8, 9 or 10 basic amino acid residues. In particular embodiments, one or both of $R^1$ is a palmitoyl group.

In another embodiment of the invention, the cationic phospholipid has the structure of Formula II, Formula II

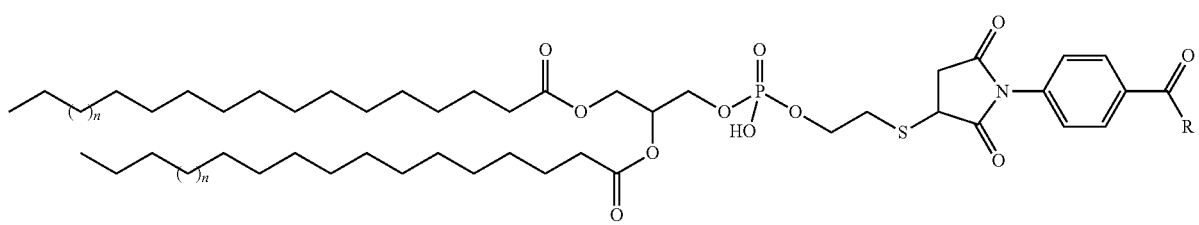

wherein each n is independently 0, 1 or 2, and R is a linear chain of between 1 and 10 basic amino acid residues, in particular arginine, lysine, or histidine, or a combination thereof. In certain embodiments, the linear chain of basic amino acid residues is a peptide of 2, 3, 4, 5, 6, 7, 8, 9 or 10 basic amino acid residues.

In certain embodiments, the cationic phospholipid of the invention has the structure of Compound 1, which is composed of a dipalmitoyl phospholipid and four arginine residues.

combination thereof. The phospholipid may be salted or desalted; hydrogenated or partially hydrogenated; or natural, semi-synthetic, or synthetic. Exemplary phospholipids suitable for use in the sterically stabilized nanocarrier of this invention include dimyristoyl-glycero-phosphoethanolamine (DMPE), dipalmitoylglycerophosphoethanolamine (DPPE), distearoylglycerophosphoethanolamine (DSPE), and dioleolyl-glycero-phosphoethanolamine (DOPE). The nature of these phospholipids will allow their degradation at Compound 1

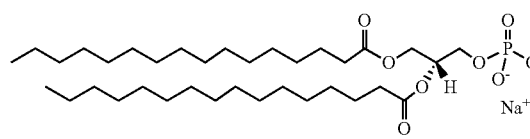
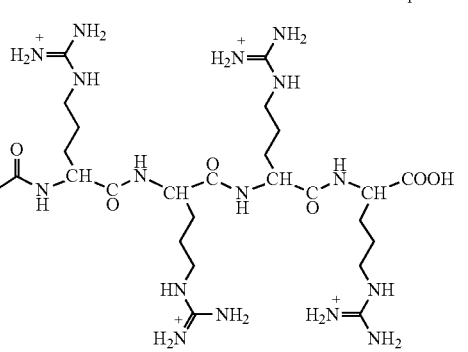

A cationic phospholipid of this invention can be synthesized as described herein or by any conventional method for covalently attaching a peptide to a lipid. In certain embodiments, the phospholipid is covalently attached to an amino acid or peptide via a bifunctional group, e.g., a heterobifunctional group, as described herein. The cationic phospholipid of this invention can be prepared and provided in a pharmaceutically acceptable carrier or in lyophilized form. In certain embodiments, the cationic phospholipid is provided in a kit for preparing a sterically stabilized nanocarrier.

Advantageously, cationic phospholipids, such as compound 1, facilitate the delivery and uptake of nucleic acid-based therapeutics into cells. Therefore, the cationic phospholipids of this invention find particular use in the preparation of a sterically stabilized nanocarrier containing the cationic phospholipid and a PEGylated phospholipid. As used herein, a sterically stabilized nanocarrier, sterically stabilized nanoparticle (SSNP) or sterically stabilized phospholipid nanoparticle (SSLNP) are used interchangeably herein to refer to a self assembly of phospholipids into a nanoparticle having a size of about 10 to about 100 nm. Advantageously, SSLNPs can diffuse through liver sinusoids, renal basal membrane fenestrations and extracellular matrix due to their small particle size, and to be taken up by hepatocytes through receptor-mediated endocytosis, facilitated by a conjugated targeting ligand.

With reference to the PEGylated phospholipid of the nanocarrier, said phospholipid can be any of various phosphorus-containing lipids that are composed mainly of fatty acids, a phosphate group, and a simple organic molecule such as glycerol. Representative phospholipids include, for example, phosphatidylcholine, phosphatidylethanolamine, diacyl-glycero-phosphoethanolamines such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE), phosphatidylserine, phosphatidylinositol, phosphatidylglycerol, phosphatidic acid, lysophospholipids, egg or soybean phospholipid or a endosomal pH and enzymatic environment releasing the encapsulated active material into the cytoplasm for its intended purpose.

Advantageously, the PEGylated phospholipid of the sterically stabilized nanocarrier prevents the interaction of the nanomedicine with bloodstream opsonins and uptake by reticulo-endothelial system (RES) organs. Furthermore, PEG provides functional groups for the conjugation of targeting ligands to achieve tissue specificity. A PEGylated phospholipid refers to an amphiphilic block copolymer composed of polyethylene glycol (PEG) and a phospholipid. The molecular weight of the PEG may vary from about 200 to about 50,000. Representative commercially available PEG includes PEG 350, PEG 750, PEG 1000, PEG 2000, PEG 3000 and PEG 5000. Generally, it has been found that increasing the molecular weight of the PEG reduces the concentration of the stabilizing component required to achieve stabilization. In one embodiment, the PEG is PEG 2000.

PEG can be conjugated to a phospholipid using standard coupling reactions known to and used by those of skill in the art. In addition, preformed PEG-phospholipid conjugates are commercially available from a variety of vendors. A preferred PEGylated phospholipid is DSPE-PEG$_{2000}$.

The sterically stabilized nanocarrier of the invention is prepared by mixing the phospholipid, in particular a PEGylated phospholipid, with a cationic phospholipid as described herein under conditions suitable for self-association. As described in the Example 1, the film rehydration method as suitable for providing sterically stabilized nanocarrier compositions. In certain embodiments, the N/P ratio used in the preparation of the nanocarrier of this invention is in the range of 5 to 50. In particular embodiments, the N/P ratio is in the range of 10 to 30. In a preferred embodiment, an N/P ratio of 30 is used.

As indicated, the sterically stabilized nanocarrier of this invention can provide passive delivery (i.e., not targeted to a particular cell or tissue) or targeted delivery into a particular cell or tissue type. In accordance with embodiments pertaining to targeted delivery, the nanocarrier further includes a targeting ligand. The targeting ligand can be attached or appended to the PEGylated phospholipid or cationic phospholipid such that the ligand is presented on the surface of the nanocarrier. In particular embodiments, the targeting ligand can be attached or appended to the PEG component of the PEGylated phospholipid. The expression "targeting" used in conjunction with "agent" or "ligand" (for uses in targeted delivery systems) refers to a compound which is capable of interacting with a complementary binding moiety at a desired location and/or under desired conditions. For example, complementary binding moieties can be ligands and anti-ligands (e.g., streptavidin and biotin, protein A or G and Fc region of immunoglobulins), ligands and receptors (e.g., small molecule ligands and their receptors, or sugar-lectin interactions), phage display-derived peptides, complementary nucleic acids (e.g., DNA hybrids, RNA hybrids, DNA/RNA hybrids, etc.), and aptamers. Other exemplary complementary binding moieties include, but are not limited to, moieties exhibiting complementary charges, hydrophobicity, hydrogen bonding, covalent bonding, Van der Waals forces, reactive chemistries, electrostatic interactions, magnetic interactions, etc.

A "targeting ligand" or "targeting agent" specific for a particular receptor refers to a compound, which is a specific binding partner of a specific binding pair, wherein the other binding partner is a receptor. The receptor may be attached to a cell membrane or surface or in soluble form and may be present intracellularly and/or extracellularly in a subject, preferably a mammalian subject, e.g., a human or animal. Examples of a receptor include, without limitation, membrane receptors, soluble receptors, cloned or recombinant receptors, hormone receptors, drug receptors, transmitter receptors, autocoid receptors, cytokine receptors, antibodies, adhesion molecules, agglutinins, integrins, and selectins. Typically, the binding affinity of a targeting ligand for its receptor may be at least $10^{-5}$ M, preferably $10^{-7}$ M or greater, e.g., in the range of $10^{-8}$ M to $10^{-12}$ M.

Examples of targeting ligands include, without limitation, a peptide including derivatives thereof such as aza-peptide derivatives or derivatives containing partially or only D-amino acids or a glycopeptide; a protein, including a glycoprotein or phosphoprotein; a carbohydrate; glycolipid; phospholipid; oligonucleotides; polynucleotide; aptamers; spiegelmers; a vitamin (e.g., vitamin B9 or folic acid, vitamin B12); antigens and fragments thereof; haptens; receptor agonists; partial agonists; mixed agonists; antagonists; drugs; chemokines; hormones (e.g., LH, FSH, TRH, TSH, ACTH, CRH, PRH, MRH, MSH, glucagon, prolactin); transferrin; lactoferrin; angiotensin; histamine; insulin; lectins; transmitters; autocoids; growth factors (e.g., PDGF, VEGF, EGF, TGFa, TBFB, GM-CSF, G-CSF, M-CSF, FGF, IGF, bombesins, thrombopoietin, erythropoietin, oncostatin and endothelin 1); cytokines including interleukins (e.g., interleukins 1 to 15); lymphokines and cell signal molecules such as tumor necrosis factor (e.g., tumor necrosis factors α and β) and interferons (e.g., interferons α, β and γ); prosthetic groups; coenzymes; cofactors; regulatory factors; or any other naturally occurring or synthetic organic molecule that can specifically bind to a receptor, including fragments, analogs and other derivatives thereof that retain the same binding properties. In a preferred embodiment, the targeting ligand is galactosamine.

Peptides serving as targeting ligands can be composed of from 1 to 30, preferably of 2 to 20, most preferably of 3 to 10 amino acid residues and can include natural occurring L-amino acids, D-amino acids, synthetic amino acids, beta amino acids and homologues thereof. Peptides are typically connected through their N-terminus, C-terminus and/or through their side chains to reactive groups on the surface of the nanocarrier. Furthermore, peptides may bear protecting groups at the N-terminus, C-terminus and in the side chains. Exemplary peptides for use in the present application include, e.g., cell-specific ligands such as the Arg-Gly-Asp peptide, Asn-Gly-Arg peptide, Ala-Thr-Trp-Leu-Pro-Pro-Arg peptide (SEQ ID NO:1), Ala-Pro-Arg-Pro-Gly peptide (SEQ ID NO:2), Ser-Met-Ser-Ile-Ala-Arg-Leu peptide (SEQ ID NO:3), Thr-Ala-Ala-Ser-Gly-Val-Arg-Ser-Met-His peptide (SEQ ID NO:4), Leu-Thr-Leu-Arg-Trp-Val-Gly-Leu-Met-Ser peptide (SEQ ID NO:5), Cys-Asp-Ser-Asp-Ser-Asp-Ile-Thr-Trp-Asp-Gln-Leu-Trp-Asp-Leu-Met-Lys peptide (SEQ ID NO:6), Gly-Pro-Leu-Pro-Leu-Arg peptide (SEQ ID NO:7), His-Trp-Gly-Phe peptide (SEQ ID NO:8) and derivatives thereof. Another exemplary peptide includes Vasoactive Intestinal Peptide (His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn; SEQ ID NO:9), which directly targets liver HSC.

The choice of a targeting ligand for use in the present invention will be determined by the cell or tissue to be targeted as well as the nature of the disease, condition, or infection to be assayed and/or treated. Likewise, the choice of conjugation (or coupling) method of the targeting ligand to a molecule of the nanocarrier (i.e., a phospholipid, PEGylated phospholipid or cationic phospholipid) depends on various factors, such as the nature of the ligand to be attached, i.e., physical attributes (e.g., size, charge, etc.), the nature of the reactive groups present on the targeting ligand, and the like. In some embodiments, conjugation is carried out in the presence of a bifunctional agent (i.e., an agent with two functional (end) groups), or a heterobifunctional agent (i.e., an agent with two different functional (end) groups). The use of such a (hetero)bifunctional agent results in a lipid-ligand conjugate wherein lipid and ligand may be directly linked to each other or separated by a spacer (e.g., PEG). Typical functional groups include, but are not limited to, groups such as succinimidyl esters, maleimides, and pyridyldisulfides. In some embodiments, the bifunctional agent is selected from, but not limited to, e.g., carbodiimides, N-hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), N-Succinimidyl 3-[2-pyridyldithio]-propionamido (SPDP), succimidyl a-methylbutanoate, biotinamido-hexanoyl-6-amino-hexanoic acid N-hydroxy-succinimide ester (SMCC), succinimidyl-[(N-maleimidopropionamido)-dodecaethyleneglycol]ester (NHS-PE012), N-succinimidyl (4-iodoacetyl) aminobenzoate (SIAB), N-succinimidyl S-acetylthioacetate (SATA), m-maleimidobenzoyl-N-hydroxysuccinimide ester (MBS) and N-D-maleimidobutyryloxy-succinimide ester (GMBS), succinimidyl dicarbonyl pentane or disuccinimidyl suberate. Preferred conjugation methods include carbodiimide-mediated amide formation and active ester maleimide-mediated amine and sulfhydryl coupling, and the like.

Polypeptides can conveniently be conjugated to a lipid (e.g., PEGylated phospholipid) via amine or thiol groups in lysine or cysteine side chains respectively, or by an N-terminal amino group. Likewise, oligonucleotides can conveniently be conjugated to a lipid (e.g., PEGylated phospholipid) through a unique reactive group on the 3' or 5' end, e.g., a sulfhydryl, amino, phosphate group or the like. These and other conjugation techniques are known in the art (see, e.g., U.S. Pat. No. 5,512,439; WO 01/22995; Greg Hernanson (1996) *Bioconjugate Techniques*, Academic Press).

For the purposes of the present invention, the sterically stabilized nanocarrier can be prepared with or without a therapeutic agent. However, in particular embodiments, the nanocarrier of the invention includes a therapeutic agent. In certain embodiments, the therapeutic agent is a negatively charged therapeutic polymer encapsulated within an aqueous interior of the nanocarrier. In other embodiments, the nanocarrier of the invention includes a nucleic acid as a therapeutic agent. As used herein, the term "nucleic acid" is meant to include any oligonucleotide or polynucleotide. The terms "polynucleotide" and "oligonucleotide" herein refer to a polymer or oligomer of nucleotide or nucleoside monomers composed of naturally occurring bases, sugars and inter-sugar (backbone) linkages. The terms "polynucleotide" and "oligonucleotide" also include polymers or oligomers composed of non-naturally occurring monomers, or portions thereof, which function similarly. Such modified or substituted oligonucleotides are often preferred over native forms because of properties such as, for example, enhanced cellular uptake and increased stability in the presence of nucleases.

Oligonucleotides may be oligodeoxyribonucleotides, oligoribonucleotides or a combination thereof. An oligodeoxyribonucleotide is composed of a deoxyribose joined covalently to phosphate at the 5' and 3' carbons of this sugar to form a negatively charged alternating, unbranched polymer. An oligoribonucleotide is composed of a similar repeating structure where each nucleotide has a ribose sugar group. Modified ribose molecules may also be included in an oligoribonucleotide.

The nucleic acid that is present in a sterically stabilized nanocarrier of this invention includes any form of nucleic acid that is known. The nucleic acids used herein can be single-stranded DNA or RNA, or double-stranded DNA or RNA, or DNA-RNA hybrids or RNA-Peptide nucleic acid (PNA) and/or DNA-PNA hybrids or PNA duplexes. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense molecules, ribozymes, microRNA, and triplex-forming oligonucleotides.

Nucleic acids may be of various lengths, generally dependent upon the particular form of nucleic acid. For example, in particular embodiments, plasmids or genes may be from about 1,000 to 100,000 nucleotide residues in length. In particular embodiments, oligonucleotides may range from about 10 to 100 nucleotides in length. In various related embodiments, oligonucleotides, whether single-stranded, double-stranded, and triple-stranded, may range in length from about 10 to about 50 nucleotides, from about 21 to about 50 nucleotides, from about 15 to about 30 nucleotides, from about 20 to about 30 nucleotides in length. Polynucleotides of 50 nucleotides or less are generally termed "fragments".

In particular embodiments, an oligonucleotide (or a strand thereof) may specifically hybridize to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a reduction or loss of utility or expression therefrom, and there is a sufficient degree of specific base-pairing to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted.

In some embodiments, sterically stabilized nanocarriers include RNA interference (RNAi) molecules. RNA interference methods using RNAi molecules can be used to disrupt the expression of a gene or polynucleotide of interest. Small interfering RNA (siRNA) are RNA duplexes normally 15-30 nucleotides long that can associate with a cytoplasmic multi-protein complex known as RNAi-induced silencing complex (RISC). RISC loaded with siRNA mediates the degradation of homologous mRNA transcripts; therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense oligonucleotide or ribozymes. RNAi reagents may include DNA sense:RNA antisense hybrids, RNA sense:DNA antisense hybrids, and DNA:DNA hybrids are capable of mediating RNAi. Thus, RNAi molecules containing any of these different types of double-stranded molecules may be used. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded polynucleotides composed of two separate strands, i.e., a sense strand and an antisense strand, e.g., siRNA; polynucleotides containing a hairpin loop of complementary sequences, which forms a double-stranded region, e.g., shRNAi molecules; and expression vectors that express one or more polynucleotides capable of forming a double-stranded polynucleotide alone or in combination with another polynucleotide.

RNA interference may be used to specifically inhibit expression of target polynucleotides. Double-stranded RNA-mediated suppression of gene and nucleic acid expression may be accomplished according to the invention by introducing dsRNA, siRNA or shRNA into cells or organisms. siRNA may be double-stranded RNA, or a hybrid molecule comprising both RNA and DNA, e.g., one RNA strand and one DNA strand, or sisiRNA.

RNAi molecules targeting specific polynucleotides can be readily prepared according to procedures known in the art. Accordingly, one skilled in the art would understand that a wide variety of different siRNA molecules may be used to target a specific gene or transcript. In certain embodiments, siRNA molecules according to the invention are double-stranded and 16-30 or 18-25 nucleotides in length, including each integer in between.

Generally, siRNA molecules are completely complementary to one strand of a target DNA molecule. In other embodiments, siRNAs may have a modified composition, such as, for example, 2'-deoxy or 2'-O-methyl modifications. However, in preferred embodiments, the entire strand of the siRNA is not made with either 2' deoxy or 2'-O-modified bases.

Lipid nanoparticle-mediated gene transfection for the treatment of genetic and metabolic disorders or tumors has moved to clinical trial phases. For example, a phase I pilot study of gene therapy for cystic fibrosis using cationic liposome-mediated gene transfer (NCT00004471) has been completed. Further, a phase I trial of intratumoral epidermal growth factor receptor (EGFR) antisense DNA delivered by DC-Chol liposomes in advanced head and neck cancer, including oral squamous cell carcinoma (NCT00009841)

has also been carried out. Examples of RNAi therapies that have been or are being analyzed in clinical trials and therefore of use in combination with the instant nanocarrier are listed in Table 1. In general, the present invention is application to the delivery of a variety of nucleic acid molecules used in the treatment of diseases or conditions such as genetic or metabolic disorders, chronic inflammatory disorders or cancer.

TABLE 1

| Clinical Setting | Drug | Indication(s) | Target(s) | Sponsor |
|---|---|---|---|---|
| Ocular and retinal disorders | TD101 | Pachyonychia congenita | Keratin 6A N171K mutant | Pachyonychia Congenita Project |
| | QPI-1007 | Non-arteritic anterior ischaemic optic neuropathy | Caspase 2 | Quark Pharm., Inc. |
| | AGN211745 | Age-related macular degeneration; choroidal neovascularization | VEGFR1 | Sirna Therapeutics Inc. |
| | PF-655 | Diabetic macular oedema (DME); age-related macular degeneration (AMD) | RTP801 | Quark Pharm., Inc. |
| | SYL040012 | Glaucoma | β2 adrenergic receptor | Sylentis |
| | Bevasiranib | Diabetic macular oedema | VEGF | Opko Health, Inc. |
| | Bevasiranib | Macular degeneration | VEGF | Opko Health, Inc. |
| Cancer | CEQ508 | Familial adenomatous polyposis | β-catenin | MDRNA, Inc. |
| | ALN-PLK1 | Liver tumors | PLK1 | Alnyam Pharm. |
| | FANG | Solid tumors | Furin | Gradalis, Inc. |
| | CALAA-01 | Solid tumors | RRM2 | Calando Pharm. |
| | SPC2996 | Chronic myeloid leukemia | BCL-2 | Santaris Pharm. |
| | ALN-VSP02 | Solid tumors | VEGF, kinesin spindle protein | Alnylam Pharm. |
| | NCT00672542 | Metastatic melanoma | LMP2, LMP7, and MECL1 | Duke University |
| | Atu027 | Advanced, recurrent or metastatic solid malignancies | PKN3 | Silence Therapeutics |
| Kidney disorders | QPI-1002/I5NP | Acute kidney injury | p53 | Quark Pharm., Inc. |
| | QPI-1002/I5NP | Delayed graft function kidney transplant | p53 | Quark Pharm., Inc. |
| | QPI-1002/I5NP | Kidney injury acute renal failure | p53 | Quark Pharm., Inc. |
| LDL lowering | TKM-ApoB | Hypercholesterolaemia | APOB | Tekmira Pharm. Corp. |
| | RO-040,201 | Hypercholesterolaemia | APOB | Tekmira Pharm. Corp. |
| Antiviral | SPC3649 | Hepatitis C virus | miR-122 | Santaris Pharm |
| | pHIV7-shI-TAR-CCR5RZ | HIV | HIV Tat protein, HIV TAR RNA, human CCR5 | City of Hope Medical Center/Benitec |
| | ALN-RSV01 | RSV in volunteers | RSV nucleocapsid | Alnylam Pharm. |
| | ALN-RSV01 | RSV in lung transplant patients | RSV nucleocapsid | Alnylam Pharm. |
| | ALN-RSV01 | RSV in lung transplant patients | RSV nucleocapsid | Alnylam Pharm. |

*See Davidson & McCray (2011) *Nat. Rev. Genet.* 12: 329-340.
POB, apolipoprotein B;
BCL-2, B-cell CLL/lymphoma 2;
CCR5, C-C chemokine receptor type 5;
LDL, low-density lipoprotein;
LMP2, also known as proteasome subunit beta type 9 (PSMB9);
LMP7, also known as proteasome subunit beta type 8 (PSMB8);
MECL1, also known as proteasome subunit beta type 10 (PSMB10);
Pharm., Pharmaceuticals;
PKN3, protein kinase N3;
PLK1, polo-like kinase 1;
RRM2, ribonucleoside-diphosphate reductase subunit M2;
RSV, respiratory syncytial virus;
RTP801, also known as DNA damage-inducible transcript 4 protein (DDIT4);
VEGF, vascular endothelial growth factor.

The nanocarrier of the present invention can be prepared by any conventional method. Given that phospholipids are amphiphilic structures that display physicochemical properties of naturally occurring lipids, phospholipids spontaneously form a bilayer structure upon dispersion in water, thereby entrapping or encapsulating active materials such as therapeutics within the core of the formed structure. Hence, upon mixing with a negatively charged nucleic acid, e.g., siRNA, the phospholipids spontaneous entrapment the nucleic acid through electrostatic interactions.

The nanocarrier of the invention can be formulated as a pharmaceutical composition, e.g., which further includes a pharmaceutically acceptable carrier, such as physiological saline or phosphate buffer, selected in accordance with the route of administration and standard pharmaceutical practice. Thus, a further aspect the present invention is directed toward a pharmaceutical composition containing one or more sterically stabilized nanocarriers comprising a cationic phospholipid, e.g., Compound 1, optionally in combination with other co-lipids and pharmaceutically acceptable diluents, excipients or carriers.

The term "carrier" refers to a diluent, adjuvant, or excipient, with which the instant nanocarrier is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when the nanocarrier is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

The pharmaceutical compositions of the present invention can be used in either in vitro, such as cell culture applications, or in vivo applications. With respect to in vivo applications, the formulations of the present invention can be administered to a patient in a variety of forms adapted to the chosen route of administration, including parenteral, oral, or intraperitoneal administration. Parenteral administration includes intravenous, intramuscular, interstitially, intraarterially, subcutaneous, intraocular, intrasynovial, transepithelial (including transdermal), pulmonary via inhalation, ophthalmic, sublingual and buccal, topically (including ophthalmic, dermal, ocular, rectal), and nasal inhalation via insufflation administration, preferably intravenous administration.

Pharmaceutical compositions include those wherein a therapeutic agent is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of the therapeutic agent that is sufficient to maintain therapeutic effects.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. The data obtained from such procedures can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a therapeutic agent required for use in therapy varies with the nature of the condition being treated, the length of time that activity is desired, and the age and the condition of the patient, and ultimately is determined by the attendant physician. Dosage amounts and intervals can be adjusted individually to provide plasma levels of the therapeutic agent that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. In practice, the physician determines the actual dosing regimen that is most suitable for an individual patient, which can vary with the age, weight, and response of the particular patient.

The concentration of nanocarrier in the pharmaceutical formulations can vary widely, i.e., from less than about 0.01%, usually at or at least about 0.05-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration.

Having demonstrated the uptake and delivery of a therapeutic agent, the present invention also provides a method for delivering a therapeutic agent to a subject and a method for preventing or treating a disease or condition by administering to the subject in need of treatment an effective amount of a sterically stabilized phospholipid nanocarrier composed of a PEGylated phospholipid complexed with a cationic phospholipid, e.g., Compound 1, and incorporating one or more therapeutic agents.

The nanocarriers described herein can deliver any negatively charged therapeutic polymer, such as a nucleic acid to a cell of a subject. In certain embodiments, the invention includes delivering a nucleic acid into a cell of a subject. Preferred nucleic acids are siRNA, immune-stimulating oligonucleotides, plasmids, antisense and ribozymes. The compositions of the present invention can be adsorbed to almost any cell type. Once adsorbed, the nancarrier can either be endocytosed by a portion of the cells, exchange lipids with cell membranes, or fuse with the cells. Transfer or incorporation of the nucleic acid portion of the nanocarrier can take place via any one of these pathways. Without intending to be limited with respect to the scope of the invention, it is believed that in the case of particles taken up into the cell by endocytosis, the particles then interact with the endosomal membrane, resulting in destabilization of the endosomal membrane, possibly by the formation of nonbilayer phases, resulting in introduction of the encapsulated nucleic acid into the cell cytoplasm. Similarly, in the case of direct fusion of the particles with the cell plasma membrane, when fusion takes place, the liposome membrane is integrated into the cell membrane and the contents of the liposome combine with the intracellular fluid.

Typical applications of the instant methods include using well-known procedures to provide intracellular delivery of siRNA to knock down or silence specific cellular targets. Alternatively, applications include delivery of DNA or mRNA sequences that code for therapeutically useful polypeptides.

Methods of the present invention may be practiced in vitro, ex vivo, or in vivo. For example, the compositions of the present invention can also be used for delivery of nucleic acids to cells in vivo, using methods which are known to those of skill in the art. Whether treatment is indicated depends on the individual case and is subject to medical assessment (diagnosis) that takes into consideration signs, symptoms, and/or malfunctions that are present, the risks of developing particular signs, symptoms and/or malfunctions, and other factors.

In certain embodiments, the method of the invention is for use in reversing or treating renal fibrosis, liver fibrosis or cirrhosis. Among digestive diseases, liver fibrosis and cirrhosis are the most common non-neoplastic cause of mortality in the US. Liver fibrosis and cirrhosis impose a pronounced burden on society and treatment remains an unmet medical need with no effective therapy other than liver transplant. Liver fibrosis is a consequence of wound healing responses due to chronic liver injury caused by viral, autoimmune, drug-related, cholestatic or metabolic diseases. As a result of liver injury, hepatic stellate cells are activated by CTGF, TGFβ1 and other proteins excreted by the injured hepatocytes. Subsequently, HSC transition from quiescent, vitamin A storing cells into proliferative, fibrogenic and contractile myofibroblasts. These deposit collagen in large quantities into the extracellular matrix (ECM) surrounding hepatocytes, changing the ECM quality and quantity, hence affecting liver morphology and function. Progression of the disease with sustained fibrogenesis leads to cirrhosis which in turn leads to the development of liver cancer.

CTGF protein is known to play a crucial role in chondrogenesis and angiogenesis during embryonic development. It is also a central regulator of ECM in adult tissues and organs, contributing to ECM accumulation in wound healing by promoting direct interactions among matrix components. Since both TGFβ1 and CTGF are significantly upregulated in hepatocytes and hepatic stellate cells during liver fibrosis, targeting of TGFβ1 and CTGF is of primary interest to reverse the progression of fibrosis and trigger ECM degradation. It has been shown that systemic application of TGFβ1 inhibitors is hazardous due to its importance in maintaining physiologic and pathologic functions such as tumor suppression. Therefore, targeting of CTGF is of particular interest in reversing liver fibrosis.

By specifically delivering RNAi molecules that inhibit the expression of CTGF in hepatocytes and HSC of the diseases animals, sequence-specific degradation of CTGF mRNA is achieved causing the down-modulation of CTGF protein activity. This will shift the TGF-β/BMP-7 (a natural antagonist of TGF-β) balance in the direction of anti-fibrosis, i.e., inhibiting ECM synthesis, epithelial-mesenchymal transition and HSC-activation, and increasing ECM-degradation. The beneficial effect of CTGF knockdown by RNAi in preventing and reversing liver fibrosis have been shown in fibrotic mice and rat models using polymeric transfection agents such as PEI or locally through portal vein injections (Uchio, et al. (2004) *Wound Repair Regen.* 12:60-66; Li, et al. (2006) *J. Gene Med.* 8(7):889-900; George &Tsutsumi (2007) *Gene Ther.* 14(10):790-803). In this respect, it has now been shown that siRNA targeting CTGF can deactivate hepatic stellate cells in culture and decrease the amount of collagen excreted causing the formation of a fibril extracellular matrix. Therefore, direct delivery of siRNA against CTGF to HSC and neighboring hepatocytes by the surface conjugation of Galactosamine (GalN) to nanocarriers of the present invention can also prevent or reverse liver fibrosis.

The present invention also provides for kits for preparing the nanocarriers described herein. Such kits can be prepared from readily available materials and reagents, as described above. For example, such kits can include any one or more of the following materials a cationic phospholipid (e.g., Compound 1), a phospholipid (e.g., a PEGylated phospholipid), nucleic acid (RNA, DNA, single or double-stranded), a targeting ligand, and instructions. A wide variety of kits and components can be prepared according to the present description, depending upon the intended user of the kit and the particular needs of the user. For example, the kit may contain any one of a number of targeting agents for targeting the nanocarrier to a specific cell type, as described above.

The kit may optionally include instructional materials containing directions (i.e., protocols) providing for the use of the nanocarrier for transfecting cells in vivo, ex vivo, or in vitro. Typically, the instruction materials describe the procedure for preparing the nanocarrier from lipids and nucleic acid, as described above, as well as procedures for transfecting cells.

The following non-limiting examples are provided to further illustrate the present invention.

Example 1

Materials and Methods

Materials.
1, 2-Distearoyl-sn-glycero-3-phosphatidyl-ethanolamine-N-[methoxy(polyethyleneglycol)-2000] sodium salt (DSPE-PEG$_{2000}$) was purchased from Lipoid GmbH (Ludwigshafen, Germany). 1,2-Dipalmitoyl-sn-Glycero-3-Phosphothioethanol Sodium Salt (Ptd Thioethanol) and 1,2-distearoyl-sn-glycero-3-phosphoethanolamine-N-[carboxy (polyethylene glycol)-2000] ammonium salt (DSPE-PEG$_{2000}$ Carboxylic Acid) were from Avanti Polar Lipids, Inc. (Alabaster, Ala.). D-galactosamine hydrochloride and N-(3-dimethylaminopropyl)-N'-ethylcarbodiimide (EDC) were from ThermoFisher Scientific (Pittsburgh, Pa.). N-hydroxy-succinimide (NHS), negative siRNA control and Cy5-labeled siRNA were purchased from Sigma-Aldrich (St. Louis, Mo.). siRNA against CTGF was obtained from Santa Cruz Biotechnology (Dallas, Tex.). RNASE ONE Ribonuclease, CELLTITER-96 AQ$_{ueous}$ One Solution Cell proliferation Assay and CYTOTOX-ONE Homogeneous Membrane Integrity Assay were purchased from PROMEGA, Inc. (Madison, Wis.). FAM-labeled siRNA, LIPOFECTAMINE, SYBR green II and ALEXA FLUOR 488 secondary antibody were from INVITROGEN-life technologies (Grand Island, N.Y.). Trypsin-EDTA (0.25% with 0.53 mM EDTA), Minimum Essential Media (MEM), fetal bovine serum (FBS), non-essential amino acids, antibiotic solution (penicillin 10,000 units/ml with streptomycin 10 mg/ml) and sodium pyruvate were all purchased from Mediatech-CELLGRO (Manassas, Va.). Hep-G2 cells were obtained from the American Type Culture Collection (Manassas, Va.). CTGF-ELISA kit was from Antigenix, Inc. (Huntington Station, N.Y.). Primary hepatic stellate cells (HSC) and corresponding stellate cell media (SteCM) and supplements were from SCIENCELL (Carlsbad, Calif.). Sirius red/fast green kit was from Chondrex, Inc. (Redmond, Wash.). Primary anti-collagen I, anti-collagen-III and anti- α-SMA antibodies were from Abcam (Cambridge, Mass.). All animals (6 weeks old male Balb/c mice) were obtained from Harlan Laboratories. Ketamine hydrochloride injection USP and ANASED injection (Xylazine hydrochloride) were obtained from the University of Illinois at Chicago. Other chemicals, if not specified, were purchased from Thermo-Fisher Scientific (Pittsburgh, Pa.) or Sigma-Aldrich (St. Louis, Mo.).

Preparation of Compound 1.

Compound 1 was synthesized and purified to >95% as follows. Arg-Arg-Arg-Arg (SEQ ID NO:10) peptide synthesis was performed by solid-phase peptide synthesis using Fmoc-AA-Wang resin (50 µmole) and SYMPHONY Peptide Synthesizer (Protein Technologies Inc., AZ). The peptide was synthesized in cycles, starting with the removal of the Fmoc group with 20% piperidine in N,N-Dimethylformamide (DMF) (2×5 minutes) followed by washing the resin with DMF (6×30 seconds). The first amino acid (Fmoc protected, 2 equiv) was added in the presence of 0.4 M O-Benzotriazole-N,N,N',N'-tetramethyl-uronium-hexafluoro-phosphate (HBTU, 1.9 equiv), and 0.8 M 4-methylmorpholine (NMM, 4 equiv) in DMF (3×30 minutes), amino acids were added in cycles. Excess reagents were washed (6×30 seconds) with DMF. The synthesis took place from C-terminus to N-terminus with amino acids side groups protected during synthesis. For the coupling of the Arg-Arg-Arg-Arg (SEQ ID NO:10) peptide to the phospholipid, resin was washed with 0.5% N,N-Diisopropylethylamine (DIEA) in DMF (5×1 ml). m-Maleimidobenzoyl-N-hydroxysuccinimide ester (MBS, 1.1 equiv) and DIEA (1.1 equiv) in 1 ml DMF were added to the resin and stirred for 2 hours at room temperature. The second coupling was done with the same amounts of reagents, stirred at 4° C., overnight. Resin was then washed with DMF (5×1 ml). Ptd Thioethanol Lipid (1.1 equiv) was dissolved in chloroform and was added to the resin along with 1.1 equiv of DIEA. The reaction was run for several hours at room temperature. A second coupling was done with the lipid to ensure the reaction had gone to completion. The resin was then washed with DMF (5×1 ml) and methylene chloride (5×1 ml) and dried. The conjugated peptide was cleaved from the resin with 100% trifluoroacetic acid (TFA) for 1.5 hours and the product was purified by reversed-phase HPLC (VYDAC, Protein and peptide C18) then identified by matrix-assisted laser desorption/ionization time-of-flight mass spectrometry (MALDI-TOF MS).

Galactosamine-DSPE-PEG$_{2000}$ Coupling.

Galactosamine coupling to DSPE-PEG$_{2000}$ was performed through carboxylic acid/amine conjugation using 1-ethyl-3-(3-dimethylaminopropyl)carbodiimide (EDC) and N-hydroxysuccinimide (NHS) coupling reagents. Briefly, DSPE-PEG$_{2000}$-COOH (1 equiv) was activated by the reaction with EDC (10 equiv) in 2 ml dimethyl sulfoxide (DMSO) for 2 hours at room temperature. NHS (10 equiv) was then added to the mixture and stirred overnight at room temperature. D-Galactosamine HCl (2 equiv) was reacted with triethylamine (2 equiv) overnight at room temperature to produce the free base. D-Galactosamine base was then added to the activated DSPE-PEG$_{2000}$-COOH and the obtained powder was evaluated for successful conjugation using MALDI-TOF MS and NMR spectra.

Preparation of siRNA-SSLNP Complexes.

siRNA-SSLNP complexes were prepared by film rehydration method with different nitrogen to phosphate (N/P) ratios (30, 20 and 10). Briefly, Compound 1 and DSPE-PEG$_{2000}$ were dissolved separately in methanol then mixed in round bottom flasks at appropriate ratios. The solvent was subsequently removed using a vacuum rotary evaporator (BUCHI Labortechnik AG; Flawil, Switzerland) under a stream of argon and vacuum (600 mm Hg pressure) at 50° C. and 150 rpm for 30 minutes. The residual solvent from the resulting film was removed under vacuum overnight in the dark. Thereafter, the dried film was rehydrated with 5 nmol of siRNA in nuclease-free water. The resulting dispersion was vortexed until the film was dissolved, followed by bath sonication for 5 minutes. Flasks were then flushed with argon, sealed, and allowed to equilibrate in the dark for 2 hours at 37° C. with continuous stirring to produce siRNA-SSLNP. Samples were then extruded through Nylon membranes with pore sizes of 200, 100 and 50 nm to ensure uniformity and a particle size of <100 nm. To achieve 10% galactosamine targeting, appropriate amounts of DSPE-PEG$_{2000}$-GalN were incubated with the preformed particles and allowed to self-associate to obtain the targeted formulation (siRNA-SSLNP-GalN). Empty, sterically stabilized mixed micelles (SSMM) were prepared using equal ratios of Compound 1 and DSPE-PEG$_{2000}$ following the same procedure described above and reconstituted with siRNA-free nuclease-free water.

In an alternative method for large scale production, Compound 1 is dissolved in TBA (tert-butyl alcohol), after which it is added to DSPE-PEG$_{2000}$ in water, drop-wise, with continuous mixing under controlled conditions. The mixture is then lyophilized to produce the lipid kit, to which therapeutic agent can be added immediately before administration or use in vitro.

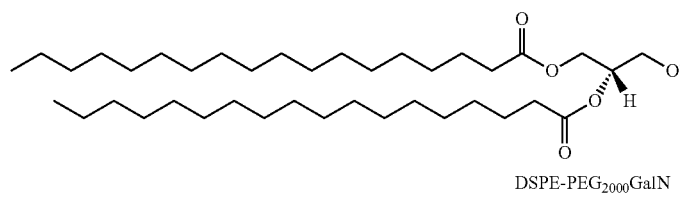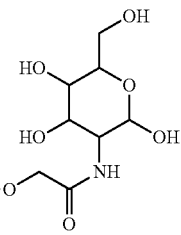

DSPE-PEG$_{2000}$GalN

Physicochemical Characterization.

Physicochemical characterization was performed through particle size distribution, mean hydrodynamic diameters and zeta potential measurements. siRNA encapsulation efficiency and protection against RNase degradation within SSLNPs and SSLNP-GalN were also evaluated using gel retardation technique and quantified by SYBR Green-II exclusion assay.

Particle size distribution and zeta potential of the prepared samples were measured using dynamic light scattering (DLS) and electrophoretic light scattering (ELS), respectively by the particle sizer (Agilent 7030 NICOMP DLS/ZLS, Santa Clara, Calif.) equipped with a 100 mW He—Ne laser (excitation at 632.8 nm) set up at a fixed scattering angle of 90°. Solvent viscosity and refractive index of water were used with values of 0.933 cP, and 1.333, respectively. Samples were measured at room temperature 25° C. and 1 atm pressure. The mean hydrodynamic particle diameters ($\bar{d}_h$) in aqueous dispersions were obtained from the Stokes-Einstein relation using the measured diffusion of particles in solution, while zeta potential $\iota$ was determined using the Smoluchowski approximation. The reported experimental results were the average of at least three values obtained from analysis of the autocorrelation function accumulated for at least 15 minutes.

Transmission electron microscope (TEM) images of the prepared siRNA-SSLNP and siRNA-SSLNP-GalN were acquired using a JOEL JEM-1220 transmission electron microscope fitted with a tungsten electron source. Briefly, freshly prepared siRNA-SSLNP complexes (5 µl) were dropped onto 300-mesh formvar carbon-coated grids (Electron Microscopy Sciences; Hatfield, Pa.) and allowed a short incubation (5 minutes) at room temperature. Negative staining was performed with 0.5% uranyl acetate (40 µl) and samples were air dried. All images were acquired at an accelerating voltage of 80 kV. Gatan Es1000W 11MP CCD camera and Digital Micrograph software was used to capture and analyze the resulting images.

For gel retardation studies, samples containing 200 ng of siRNA, with varying N/P ratios in nuclease-free water, were electrophoresed through 15% NOVEX TBE-urea gel (IN-VITROGEN Life Technologies; Grand Island, N.Y.) with TBE running buffer. Gels were run at a voltage of 180V for 60 minutes, then stained with 1:5000 SYBR Green-II in TBE with mild agitation for 30 minutes, after which they were photographed under UV light using BIORAD Gel-Doc imaging system (Life Science Research, Hercules, Calif.).

A SYBR Green-II exclusion assay was performed to quantify the encapsulation of siRNA within SSLNP using the fluorescence quenching method. These experiments were carried out by measuring the fluorescence intensity of siRNA-SSLNP complexes, prepared with different N/P ratios, as a result of the intercalation between siRNA and SYBR Green-II. Fluorescence was measured using 96-well plate reader BioTek Synergy4 (Winooski, Vt.) at excitation and emission wave lengths of 497 nm and 520 nm, respectively. Percent of encapsulated siRNA was determined from the relative fluorescence obtained with each sample to that of SYBR Green-II and siRNA in the absence of lipids.

Nuclease resistance of SSLNP incorporated siRNA was determined after the treatment of samples with 1 U of RNase I ribonuclease/µg siRNA for 30 minutes at 37° C. TRI-TON-X 100 (0.1%) was used to terminate RNase activity and Heparin sodium 50 U/µg siRNA was used to disassemble SSLNPs nanoparticles. Gel retardation and SYBR Green-II exclusion assays were repeated to determine the integrity of the preserved SSLNP siRNA compared to free siRNA.

In vitro Evaluation in Liver Cell Culture. Cytotoxicity and membrane integrity studies were performed on Hep-G2 cells and primary hepatic stellate cells (HSC), using MTS (3-(4, 5-dimethylthiazol-2-yl)-5-(3-carboxymethoxyphenyl)-2-(4-sulfophenyl)-2H-tetrazolium, inner salt) and lactate dehydrogenase (LDH) activity assays, respectively, upon treatment with siRNA-SSLNP in different concentrations in comparison to LIPOFECTAMINE as a control. Receptor-mediated cell uptake of the targeted formulation (siRNA-SSLNP-GalN) was measured using fluorescence-activated cell sorting (FACS) flow cytometry and compared to that of LIPOFECTAMINE (LF), free siRNA and non-targeted SSLNPs. In vitro gene silencing and the reversal of HSC activation was evaluated through the knockdown of CTGF, collagen type I and III as well as smooth muscle actin ($\alpha$-SMA) expression in Hep-G2 and HSC cultures, respectively.

Hep-G2 cells and primary HSC were seeded in 96-well plates at a density of $6 \times 10^3$ cells/well and allowed to attach for 24 hours under 37° C. and 5% $CO_2$. Hep-G2 were cultured in 100 µL/well MEM containing 10% FBS, 1 mM sodium pyruvate, 1% nonessential amino acids, 100 U/mL penicillin, and 100 µg/mL streptomycin, while primary HSC were incubated with 100 µL/well Stellate Cell Medium (SteCM) supplemented with 10% FBS, stellate cell growth supplement (SteCGS) and 100 U/mL penicillin, and 100 µg/mL streptomycin supplied by SCIECELL. For LDH assay, cells were incubated in FBS-free media. After attachment, the medium was replaced with 100 µL/well fresh media containing serial dilutions of vectors with a molar siRNA concentration ranging from 1 to 1000 nM, and incubated for 72 hours for MTS assay or overnight for LDH analysis. At the end of incubation period, Hep-G2 cells were treated with CELLTITER-96 $AQ_{ueous}$ One solution cell proliferation (MTS) assay while primary HSC were treated with CYTOTOX-ONE homogeneous membrane integrity (LDH) assay according to manufacturer's instructions. Absorbance was measured at 490 nm and fluorescence at excitation 560 nm and emission 590 nm for the two assays, respectively, using 96-well plate reader BioTek Synergy4 (Winooski, Vt.) and results were normalized to untreated control.

To assess the ability of SSLNP and SSLNP-GalN to transfect siRNA into cells in comparison to LIPO-FECTAMINE (LF), Carboxyfluorescein (FAM)-labeled siRNA was formulated in SSLNPs at N/P ratio of 30 as described above. Hep-G2 cells were seeded 6-well plate ($2 \times 10^5$ cell/well) with the supplements described earlier and incubated for 24 hours prior to transfection. Cells were treated with either free FAM-siRNA, siRNA-SSLNP, siRNA-SSLNP-GalN at siRNA concentration of 200 nM or siRNA-LF at 50 nM concentration according to manufacturer's recommendations. Treated cells were incubated overnight then washed with PBS and trypsinized. The uptake of FAM-siRNA mediated with different vectors was detected using Beckman Coulter Cyan ADP flow cytometry and analyzer (Indianapolis, Ind.).

In Vitro Evaluation in Renal Cell Culture.

Galactosamine receptor-mediated uptake of SSLNP-GalN by proximal renal tubular epithelial cells (HK-2) was determined using a human asialoglyco protein receptor (ASGPR) assay. Hep-G2 hepatoma cells were used as positive control, and MCF-7 breast cancer cells were used as negative control as they are not known to express surface ASGPR receptors. For this experiment, cell lines were seeded in T-75 culture-treated flasks with 15 ml media and incubated to reach confluency at 37° C. and 5% $CO_2$. MEM media supplemented with 10% FBS, non-essential amino acids, antibiotic solution (penicillin 10,000 units/ml with streptomycin 10 mg/ml) and sodium pyruvate was used for the attachment of Hep-G2 and MCF-7 cells while Keratinocyte Serum-Free Medium supplemented with 0.05 mg/ml bovine pituitary extract (BPE), 5 ng/ml human recombinant epidermal growth factor (EGF) and antibiotic solution (penicillin 10,000 units/ml with streptomycin 10 mg/ml) was used for HK-2 cells. Another batch of HK-2 cells was seeded as described above and treated with 3 ng/ml TGF-B1 to allow activation into fibroblasts.

Cells were analyzed for ASGPR expression using ASGPR-ELISA kit (My Biosource, Inc., San Diego, Calif.) according to the manufacture's protocol. Briefly, cells were lysed using M-Per buffer containing protease inhibitor cocktail with gentle shaking. Subsequently, the lysed cells were centrifuged for 10 minutes at 14,000 rpm at 4° C. The supernatant was incubated in pre-coated ASGPR-ELISA plates at 37° C. for 30 minutes, plates were then washed and further incubated with antibody-HRP conjugate solution for an additional 30 minutes. Plates were washed three, after which TMB substrate was added and the reaction was incubated in the dark for 20 minutes at 37° C. Stop solution was added to terminate the reaction and the optical density was measured at 450 nm using 96-well plate reader BioTek Synergy4 (Winooski, Vt.).

A standard curve was constructed using the ASGPR standard provided by MyBiosource, Inc. with a concentration range of 0-2000 ng/ml. The average of triplicate readings was recorded and data was reduced using Gen 5 data analysis software to generate a four parameter logistic (4-PL) curve-fit. ASGPR concentration in the wells was calculated using generated standard curve, and the results were normalized to the total protein in samples as measured by Bradford protein assay.

Bradford assay was used to normalize ASGPR protein to total protein in studies samples. For this, a standard curve was constructed using BSA with a concentration in the range 0-1.5 mg/ml. The average of triplicate readings was recorded and data was reduced using Gen 5 data analysis software to generate a four parameter logistic (4-PL) curve-fit. The same cell lysates that were used for the previous ELISA analysis were used to determine total protein concentration in flasks. For this, 10 µl samples were mixed with 200 µl COOMASSIE blue reagent in 96-well plate, after which the absorbance was measured at 595 nm using 96-well plate reader BioTek Synergy4 (Winooski, Vt.). Data was reduced using Gen 5 data analysis software to generate a four parameter logistic (4-PL) curve-fit. Total protein concentration was calculated using generated standard curve, and the results were used to normalize ASGPR concentration.

HK-2 renal cells were also used to assess the ability of the SSLNP formulation and SSLNP-GalN to internalize siRNA as compared with LIPOFECTAMINE (LF) as a positive control. For this, Carboxyfluorescein (FAM)-labeled siRNA was formulated in SSLNPs at N/P ratio of 30. HK-2 cells were seeded in 6-well plates at a density of $10^5$ cell/well and allowed to attach and activate to fibroblasts with 3 ng/ml TGF-β1 for 48 hours under 37° C. and 5% $CO_2$. and 1 ml/well Keratinocyte Serum-Free Medium supplemented with BPE, EGF in addition to 100 U/mL penicillin and 100 µg/mL streptomycin.

After confirmation of cell activation by light microscopy, cells were treated with one of the following formulations: free FAM-siRNA, FAM-siRNA in SSLNP, FAM-siRNA in SSLNP-GalN at siRNA concentration of 200 nM or FAM-siRNA in LIPOFECTAMINE (LF) at 50 nM concentration according to manufacture recommendations. For galactosamine receptor ligand competition assay, cells were incubated with 50 mM galactosamine for an hour before transfection. Treated cells were incubated overnight then washed with PBS and trypsinized using 0.25% Trypsin/0.53 mM EDTA solution. The cells were collected in serum-free media with 2% BSA and 2 mM EDTA and filtered into 5 ml round bottom tubes with stainer caps. The internalization of FAM-siRNA with different vectors was detected using Beckman Coulter Cyan ADP flow cytometry and analyzer (Indianapolis, Ind.).

Evaluation of Renal Cell Cytotoxicity.

Proliferation of HK-2 cells was assessed over an incubation period of 72 hours. HK-2 cells were seeded in 96-well plates at a density of $5\times10^3$ cells/well and allowed to attach for 24 hours under 37° C. and 5% $CO_2$. Cells were cultured in Keratinocyte Serum-Free Medium supplemented with 0.05 mg/ml bovine pituitary extract (BPE), 5 ng/ml human recombinant epidermal growth factor (EGF) and antibiotic solution (penicillin 10,000 units/ml with streptomycin 10 mg/ml). After overnight attachment, medium was replaced with 100 µL/well fresh media containing serial dilutions of the following formulations, with a molar siRNA concentration ranging from 1 to 1000 nM: free scrambled-siRNA, scrambled-siRNA in SSLNP (with N/P ratios of 30), scrambled-siRNA in SSLNP-GalN or scrambled-siRNA in lipofectamine (LF). Cells were incubated for 24, 48 to 72 hours at the same incubation conditions. At the end of incubation periods, MTS solution was added to wells and plates were further incubated in the dark for 3 hours after which the absorbance of formazan was measured at 490 nm using 96-well plate reader BioTek Synergy4 (Winooski, Vt.). The results were normalized to untreated control and percent of cell viability was calculated per treatment.

In Vitro Gene Knockdown and Protein Down-Regulation.

To evaluate CTGF down-regulation, Hep-G2 cells were seeded in 24-well plate at a density of 50,000 cells/well with the supplements described earlier and incubated for 24 hours prior to treatment. CTGF-siRNA complexes with SSLNP and SSLNP-GalN were prepared at N/P ratio of 30 as previously described. Cells were treated with either free CTGF-siRNA, CTGF-siRNA in SSLNP, or CTGF-siRNA in SSLNP-GalN at siRNA concentrations of 50, 100 and 200 nM, while positive control cells were treated with CTGF-siRNA in LF at 50 nM concentration according to manufacturer's recommendations. Treated cells were incubated overnight then analyzed for CTGF expression 24 hours post-transfection using CTGF-ELISA kit (Antigenix, Inc.; Huntington Station, N.Y.) according to the manufacturer's protocol. Results were normalized to total protein in samples measured by Bradford protein assay.

CTGF down-regulation was also assessed in HK-2 cells. HK-2 cells were seeded in 12-well plate at a density of 100,000 cells/well with 1 ml keratinocyte serum-free media and supplements. Cells were incubated for 48 hours at 37° C. and 5% $CO_2$ with 3 ng/ml TGF-β1. CTGF-siRNA complexes with SSLNP and SSLNP-GalN were prepared at N/P ratio of 30. Cells were treated with free CTGF-siRNA, CTGF-siRNA in SSLNP, or CTGF-siRNA in SSLNP-GalN at siRNA concentrations of 50, 100 and 200 nM. Fifty nM CTGF-siRNA in LF was used as positive control, while 200 nM scrambled siRNA in SSLNP-GalN used as a negative control.

After treatment, cells were incubated overnight then washed and re-incubated with fresh media for 48 hours to allow the down-regulation of expressed protein. After the incubation period, cells were analyzed for CTGF expression using CTGF-ELISA kit (Antigenix, Inc., Huntington Station, N.Y.) according to the manufacture's protocol. Briefly, cells were lysed using M-Per buffer containing protease inhibitor cocktail and shaken gently then centrifuged for 10 minutes at 14,000 rpm at 4° C. The supernatant was incubated in pre-coated CTGF-ELISA plates with biotin trace antibody at room temperature for 90 minutes, plates were then washed and further incubated with Streptavidin-HRP solution for 1 hour. This was followed by an additional three washing cycles, after which TMB substrate was added and incubated in dark for 30 minutes. 2N $H_2SO_4$ was used as stop solution and the optical density was measured at 450 nm using 96-well plate reader BioTek Synergy4 (Winooski, Vt.).

Standard curve was constructed using CTGF standard provided by Antigenix, Inc. with a concentration range of 0-20 ng/ml. The average of triplicate readings was recorded and data was reduced using Gen 5 data analysis software to generate a four parameter logistic (4-PL) curve-fit. CTGF concentration in wells was calculated using generated standard curve, and the results were normalized to the total protein in samples measured by Bradford protein assay.

Bradford assay was used to normalize CTGF protein to total protein in studies samples. For this a standard curve was constructed using BSA with concentration in the range 0-1.5 mg/ml. The average of triplicate readings was recorded and data was reduced using Gen 5 data analysis software to generate a four parameter logistic (4-PL) curve-fit. The same cell lysate that was used for the previous CTGF ELISA analysis was used to determine total protein concentration in wells. For this, 10 µl samples were mixed with 200 µl COOMASSIE blue reagent in 96-well plate, after which the absorbance was measured at 595 nm using 96-well plate reader BioTek Synergy4 (Winooski, Vt.). Total protein concentration was calculated using generated standard curve, and the results were used to normalize CTGF concentration in wells.

For the evaluation of collagen type I and III as well as α-SMA expression, an immunocytochemistry technique was used. Primary HSC were seeded at a density of 5,000 cells/well on a glass slide with cover in 0.25 ml/well SteCM as described earlier. After a 24-hour incubation, cells were treated with either free CTGF-siRNA or CTGF-siRNA in SSLNP at siRNA concentrations of 200 nM, while positive control cells were treated with CTGF-siRNA in LF at 50 nM siRNA concentration and incubated overnight. Cells were then washed three times with PBS with $Ca^{2+}$ and $Mg^{2+}$ (37° C.) and fixed in ice-cold methanol for 10 minutes, washed three times with PBST (0.1% TWEEN in PBS), and incubated in PBST containing 1% BSA for 30 minutes. All primary antibody (anti-collagen I, anti-collagen III and anti-α-SMA) incubations were performed overnight at 4° C. in 1% BSA in PBST. Following three PBST washes, cells were incubated with the ALEXA-FLUOR 488-conjugated secondary antibody in 1% BSA in PBST for 1 hour at room temperature and followed by three washes with PBST. Nuclei were stained with DAPI (4,6-diamidino-2-phenylindole) included in VECTASHILD mounting media. Images were acquired using an OLYMPUS IX70 inverted fluorescence microscope coupled with a QIMAGING RETIGA 1300 cooled-CCD digital camera; and processed using QCAPTURE PRO 6 software.

To measure the amount of collagen deposited in the extracellular matrix of HSC, cells were seeded in 24-well plate at a density of 50,000 cells/well 24 hours prior to treatment as described above. Cells were treated with either free CTGF-siRNA, CTGF-siRNA in SSLNP, or CTGF-siRNA in SSLNP-GalN at siRNA concentrations of 50, 100 and 200 nM, while positive control cells were treated with CTGF-siRNA in LF at 50 nM concentration and incubated overnight. Cells were then washed three times with PBS with $Ca^{2+}$ and $Mg^{2+}$ (37° C.) and fixed in ethanol for 10 minutes, then dyed with Sirius red/fast green (Chondrex, Inc.) according to the supplier's protocol. Absorbance was measured using BioTek Synergy4 plate reader at 540 nm and total collagen was normalized to total non-collagenous protein in the well.

In Vivo Biodistribution and Pharmacokinetic Studies.

Biodistribution studies were performed on 6-week-old Balb/c, male mice. Mice were randomized into four groups and treated with one of the following formulations: free Cy5 in D5W (60 µg (76 nmol)/kg), free Cy5-labeled siRNA, Cy5-labeled siRNA in SSLNP or Cy5-labeled siRNA in SSLNP-GalN with the latter three formulations administered at 1 mg (76 nmol)/kg dose calculated based on siRNA content. Formulations were injected via tail vein at 0.1 ml and mice were anesthetized via IP injection using ketamine/xylazine (90 mg/kg/3 mg/kg) then sacrificed by exsanguination at predetermined time points of 15 minutes, 1 hour, 3 hours, 6 hours, 9 hours and 24 hours. Organs (heart, spleen, lungs, kidneys and liver) as well as blood and urine were collected from each animal and photographed using XENOGEN (Caliper Life Sciences) IVIS Spectrum 100 imaging system at excitation and emission wave lengths of 640 nm and 680 nm, respectively. Fluorescence signals were quantified using Living Image 4.0 acquisition and analysis software. Blood was collected by cardiac puncture into EDTA-coated BD MICROTAINER tubes and centrifuged at 3000 rpm for 10 minutes to separate plasma. Cy5-siRNA concentration was quantified using 96-well plate reader BioTek Synergy4 (Winooski, Vt.) at excitation and emission wave lengths of 640 nm and 680 nm, respectively. siRNA serum concentration at tested time points was used to plot plasma concentration versus time curve and calculate PK parameters.

Data and Statistical Analysis.

All results are expressed as the mean±standard deviation (SD) of at least three experiments. For statistical analysis, student's t-test or one-way analysis of variance (ANOVA) were used. P-values less than 0.05 (p<0.05) are considered statistically significant.

Example 2

SSLNPs for siRNA Delivery

Dipalmitoyl phosphothioethanol was modified with the addition of a short peptide head group composed of four arginine amino acid residues. This modification was confirmed by the shift in molecular weight observed by the accumulated mass spectrum from 730 g/mol to 1552 g/mol. The final product, Compound 1, was purified using reverse-phase HPLC to >95% purity.

Galactosamine, as a targeting ligand, was attached to the far end of the PEG polymer of DSPE-PEG$_{2000}$, leaving the hydrophobic part of the lipid (DSPE) free for self-association with the bilayer of SSLNPs. DSPE-PEG$_{2000}$-GalN (molecular weight 3010) was successfully synthesized using DSPE-PEG$_{2000}$-COOH (molecular weight 2850) and Galactosamine (molecular weight 215.15), by reacting an activated amine group and carboxylic acid. Formation of the desired compound was further confirmed by MALDI-TOF mass spectroscopy. Peaks of the parental DSPE-PEG$_{2000}$ shifted to the right, at regions approximating the molecular weight of the conjugated galactosamine. The wide distribution of peaks and the unclear shift in molecular weight indicated that the DSPE-PEG$_{2000}$-COOH was not a homogenous polymer compound.

According to the acquired galactosamine $^1$H NMR spectra, a peak observed at 7.5 ppm represented hydrogen atoms of the amine group, the integration value of which was found to decrease after conjugation, indicating successful conjugation. Two characteristic large peaks of the parental DSPE-PEG$_{2000}$-COOH, one at 3.4 ppm corresponding to the methylene groups of mPEG, and another at 3.5 ppm assigned to the methoxy groups of mPEG were observed. Meanwhile, a peak at 4.0 ppm represented the end carboxylic group of DSPE-PEG$_{2000}$-COOH. As the two compounds were conjugated, the integration value of the peak at 4.0 ppm decreased while another representing amide group was observed at 3.8 ppm. Based on the relative integration values of the characteristic peak at 3.8 ppm, it was calculated that 30% of the DSPE-PEG$_{2000}$-COOH was successfully conjugated to galactosamine.

The particle size distribution of different siRNA formulations was evaluated, using dynamic light scattering, by volume weighted Nicomp analysis. Free siRNA (5 nmol/ml) particle size distribution showed a peak between 2-3 nm representing the small size of siRNA molecules. When complexed with LIPOFECTAMINE, Nicomp distribution showed the average hydrodynamic diameter of conventional liposomes ranging from 200 to 300 nm. The mixture of DSPE-PEG$_{2000}$ and Compound 1 in the absence of siRNA was used as a negative control, and was found to form particles of approximately nm in diameter. These were identified as sterically stabilized mixed micelles (SSMM) and were also found in all the other preparations as they were prepared in the presence of excess lipid mixture.

Three formulations were prepared with siRNA and the two lipids (DSPE-PEG$_{2000}$ and Compound 1) using N/P ratios of 10, 20 and 30. Bimodular particle size distribution was observed, one of which was identified as the SSMM peak seen earlier in the negative control sample. Peaks representing the hydrodynamic diameter of siRNA-SSLNP were found to shift to smaller values as the N/P ratio increased (Table 2).

TABLE 2

| Formulation | Particle Size (nm) | Zeta Potential (mV) in water | siRNA Loading (nmol/ml) | siRNA EE % |
|---|---|---|---|---|
| Free siRNA | 2.5 ± 1.3 | −42.48 | 5 | — |
| SSMM | 18 ± 2.8 | −1.1 | — | — |
| SSLNP (N/P = 10) | 98 ± 15 | 2.07 | 5 | 36 ± 12 |
| SSLNP (N/P = 20) | 92 ± 13 | 2.9 | 5 | 62 ± 20 |
| SSLNP (N/P = 30) | 83 ± 13 | 6.33 | 5 | 85 ± 16 |
| siRNA-LIPOFECTAMINE | 236 ± 88 | 30.99 | 5 | — |

Values are mean ± SD.
EE, encapsulation efficiency.

Particle zeta potentials showed close to neutral surface charge (Table 2) as compared to the distinct net negative and positive charges of free siRNA (−42.48 mV) and siRNA-LIPOFECTAMINE complex (30.99 mV), respectively, indicating efficient encapsulation and shielding of the charges with the exterior PEG layer. The high cationic surface charge observed with siRNA-LIPOFECTAMINE sample could be explained by the high liposome to siRNA ratio, in which the amount of interacting siRNA was not sufficient to neutralize the surface charge. In addition, this excess surface charge was utilized to achieve cell membrane interaction and internalization of LIPOFECTAMINE-siRNA complex.

A physicochemical characterization was performed to determine the location of siRNA within the formed particles and quantify the amount incorporated during its preparation. Gel electrophoresis of the prepared samples, compared to naked siRNA sample, confirmed the complexation of siRNA with SSLNPs in all three tested N/P ratios. Naked siRNA was able to travel freely toward the positively charged anode during electrophoresis, while encapsulated siRNA remained in wells. Empty SSMMs did not show any significant interaction with SYBR Green-II and were used as a negative control. Gel analysis also demonstrated the siRNA encapsulation ability of the three different SSLNP formulations at various N/P ratios, as the intensity of the migrating siRNA band decreased with increasing N/P ratio. Samples prepared with LIPOFECTAMINE showed complete complexation of siRNA to the surface of liposomes as no migrating band was observed.

Following gel electrophoresis, SYBR-Green II exclusion assay was performed to quantify the amount of siRNA encapsulated in the prepared formulations. The amount of sample to be tested was determined according to siRNA-SYBR Green-II standard curve that demonstrated a linear relationship at siRNA concentrations below 3 µg/ml. This analysis indicated that as the N/P ratio of SSLNP complexes increased, the relative fluorescence decreased, indicating a maximum binding of 85% of total siRNA at N/P ratio of 30. On the other hand, N/P ratios of 20 and 10 resulted in a decrease of total fluorescence up to 62% and 36%, respectively. siRNA encapsulation efficiency was calculated from the relative measured fluorescence to be 4.25 nmol siRNA/0.8 µmol Compound 1 with SSLNP formulation at N/P ratio of 30.

Preformed siRNA-SSLNP was incubated with galactosamine coupled DSPE-PEG$_{2000}$ to provide galactosamine as a surface targeting ligand. Samples were reevaluated for particle size and shape as well as surface charge and encapsulation efficiency. This analysis indicated that the conjugation of galactosamine did not result in a significant change in the physicochemical properties of the carrier. Particle size distribution showed a siRNA-SSLNP-GalN peak around 91±13 nm which was confirmed with TEM imaging. Zeta potential had a value of −2.53 mV and the encapsulation efficiency ranged from 73-93%. The slight increase in diameter could be attributed to the conjugation of galactosamine molecules to the far end of DSPE-PEG$_{2000}$ and their extension from the outer surface of the nanoparticles. This also explained the slight decrease in zeta potential, as galactosamine is characterized by the presence of multiple hydroxyl functional groups around its sugar ring.

Figure 2:
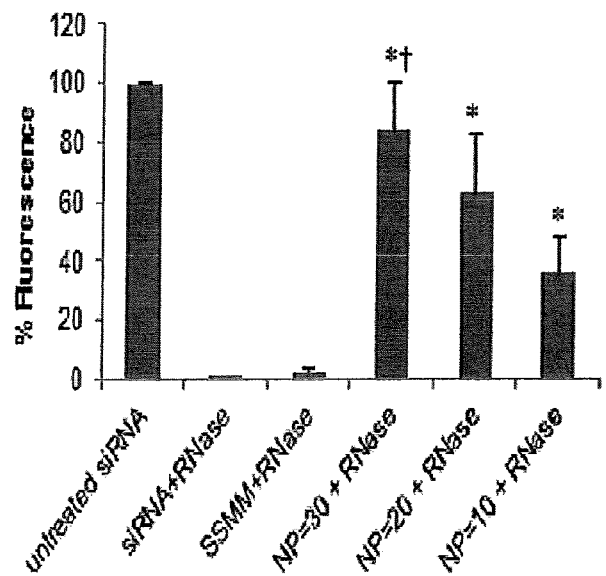
FIG. 2 shows fluorescence intensities of SSMM and siRNA-SSLNP complexes at varying N/P ratios after treatment with RNase enzyme showing percent of siRNA protected against degradation. *$p<0.05$ vs free RNase treated siRNA, † $p>0.05$ vs free siRNA control.

The ability of SSLNPs to protect siRNA against RNase enzymatic degradation was evaluated against naked siRNA. As shown in FIG. 2, after a 30 minute incubation with RNase I, naked siRNA was completely digested with no band detected on gel electrophoresis. On the contrary, an siRNA band with an intensity close to that of the untreated siRNA control was detected with the SSLNP formulation of N/P=30, confirming that this preparation was a suitable formulation for siRNA delivery. Particle size, zeta potential and the encapsulation efficiency remained unchanged after GalN surface conjugation. TEM images also confirmed the overall spherical shape of siRNA-SSLNP and average diameters of the formed particles.

Example 3

Evaluation of Delivery Efficiency and Cytotoxicity In Vitro

Cell Surface Receptor Expression.

Renal proximal tubular epithelial cells (RPTEC) represented by the immortalized HK-2 cells, in addition to Hep-G2 hepatoma cells, and MCF-7 breast cancer cells, were grown in culture treated flasks to reach confluency. Cells were analyzed for ASGPR expression using ASGPR-ELISA kit (My Biosource, Inc. San Diego, Calif.). ASGPR protein concentration was then calculated using generated standard curve, and the results were normalized to the total protein in flasks measured by Bradford protein assay.

This analysis indicated that both Hep-G2 and HK-2 cells were positive for the presence of surface ASGPR, although Hep-G2 cells were found to express the receptor twice as much as HK-2 cells. On the other hand, activation of HK-2 cells with TGF-β did not appear to significantly increase the expression of these receptors. Collectively, these results confirm the existence of functional ASGPR.

Renal Cell Uptake.

Renal tubular epithelial cells uptake of different formulations was assessed. Cells were treated with different formulations containing fluorescent labeled siRNA (FAM-siRNA), and incubated overnight then analyzed by FACS. The flow cytometric histograms in demonstrated significant shift with all formulations, indicating enhanced cellular uptake of the siRNA cargo. Quantification of percent siRNA-positive cells indicated that greater than 80% of the cells were positive for siRNA-SSLNP, either with or without targeting ligand, as compared to control cells, where fewer than 5% of the cells were siRNA-positive. This enhancement was comparable to that obtained with LIPOFECTAMINE. It was noted that the targeted formulation (siRNA-SSLNP-GalN) did not show a significant increase compared to the non-targeted formulation.

Receptor-mediated uptake was further investigated using flow cytometry after treating HK-2 cells in the presence of galactosamine in the culture media. This analysis indicated that the presence of excess free galactosamine in the transfection media reduced the uptake of SSLNP-GalN. Although this reduction was not significant, it indicated that galactosamine could compete with SSLNP-GalN for binding to ASGPR receptors on the cell surface.

Renal Cell Cytotoxicity.

The cytotoxicity of various siRNA formulations, in addition to empty lipid vehicle (SSMM), was evaluated for HK-2 renal tubular epithelial cells over extended periods of treatment. Cells were treated with different formulations at siRNA concentrations ranging from 1-1000 nM, equivalent to lipid a concentration between 300 nM to 300 µM calculated based on SSLNP formulation with N/P 30. Cell viability was evaluated using MTS assay at 24, 48 and 72 hours after treatment. This analysis indicated that there was no significant cytotoxic effect of the tested formulations for the first 24 hours of incubation, although at higher concentrations, above 250 nM siRNA, a negative effect of SSLNP-GalN and LIPOFECTAMINE on the viability of HK-2 was observed.

By examining cell viability after 48 and 72 hours of incubation, an increase in cell sensitivity was observed with longer incubation periods. Indeed, even free scrambled siRNA and empty lipid vehicle exhibited significant cytotoxicity after 72 hours of incubation, with approximately 60% proliferation obtained for both treatments at 1000 nM siRNA concentration. Meanwhile, $IC_{50}$ values for SSLNP, SSLNP-GalN and LIPOFECTAMINE were reached after this long incubation period, with values of 850, 800 and 700 nM siRNA, respectively. It is of note, however, that efficacy studies were performed at a concentration of 200 nM siRNA or less, with overnight incubations.

From all three cytotoxicity assays, it could be concluded that both SSLNP and SSLNP-GalN formulations were significantly less toxic than LIPOFECTAMINE, especially at high concentrations and long incubation hours. To compare the cell proliferation kinetics of different formulations, data from the three curves (24, 48 and 72 hour incubations) were plotted for all tested preparations at a selected concentration equivalent to 250 nM siRNA. This analysis indicated that LIPOFECTAMINE started to show significant toxicity at 48 hours, as indicated by a reduction in cell proliferation (77%) relative to the untreated control, while the targeted and non-targeted SSLNP formulations did not exhibit such effects.

Liver Cell Cytotoxicity.

Figure 3A:
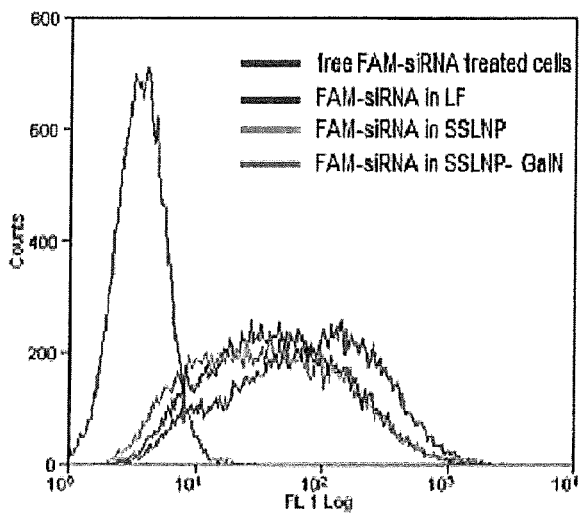
FIGS. 3A-3C show the results of cell uptake and cytotoxicity assays. Hep-G2 cell uptake of FAM-labeled siRNA in various complexes was determined.
Figure 3B:
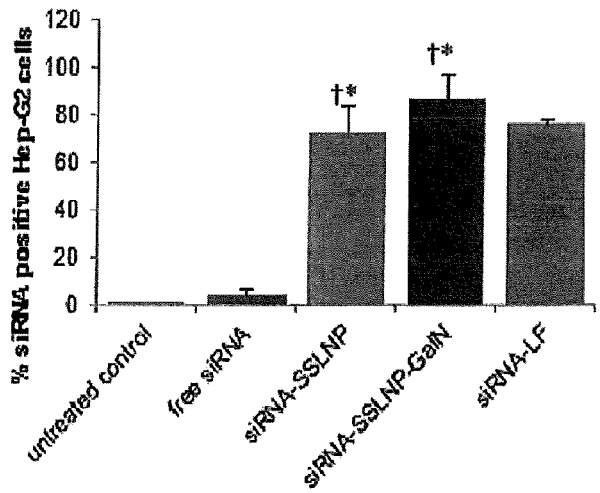

The potential of SSLNP-GalN for siRNA transfection was evaluated in vitro on Hep-G2 cells expressing asialoglycoprotein surface receptors in comparison to free siRNA and lipofectamine. The delivery efficiency was determined by FACS, which measured the number of siRNA positive cells. The flow cytometric histogram of different formulations indicated that all formulations generated a significant increase in mean fluorescence of cells as compared to non-treated cells or free siRNA treated cells (FIG. 3A). Hep-G2 cells transfected with free FAM-siRNA resulted in 3.4% siRNA positive cells, whereas SSLNP and SSLNP-GalN resulted in 73% and 87% respectively, comparable to results obtained with LIPOFECTAMINE (76%, FIG. 3B). These results indicated that targeted SSLNPs were the most efficient in delivering siRNA into cells as a result of receptor endocytosis, mediated by the interaction between galactosamine and asialoglycoprotein receptors in this case.

Figure 3C:
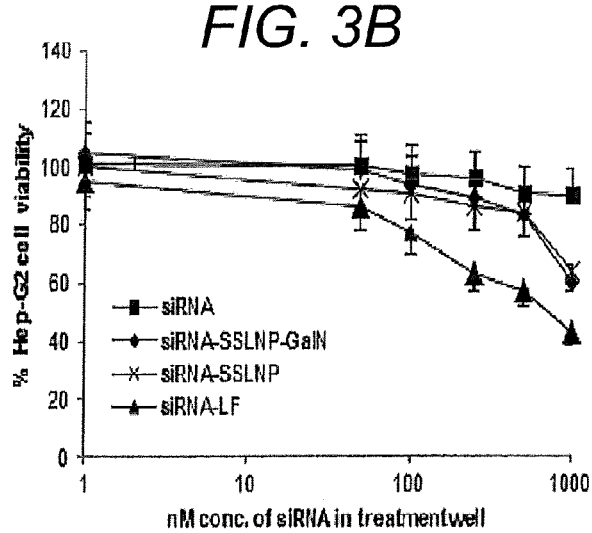

Subsequently, the cytotoxicity of the various siRNA formulations was evaluated on Hep-G2 cells and HSC. Cells were transfected with siRNA formulations at different concentrations, cells viability and membrane integrity were evaluated using MTS and LDH assays, respectively. This analysis indicated that the average cell viability observed among Hep-G2 cells transfected with SSLNPs and SSLNP-GalN was about 90% at 200 nM siRNA concentration (same concentration used for efficacy studies), versus 65% viability observed with LIPOFECTAMINE at the same siRNA concentration (FIG. 3C). Primary HSC on the other hand were found to be more sensitive to treatment, with SSLNPs affecting 25% of the cells population in comparison to LIPOFECTAMINE that resulted in more than 35% loss of membrane integrity at 200 nM siRNA concentration (FIG. 3C).

Example 4

Evaluation of Protein Down-Regulation

Figure 4:
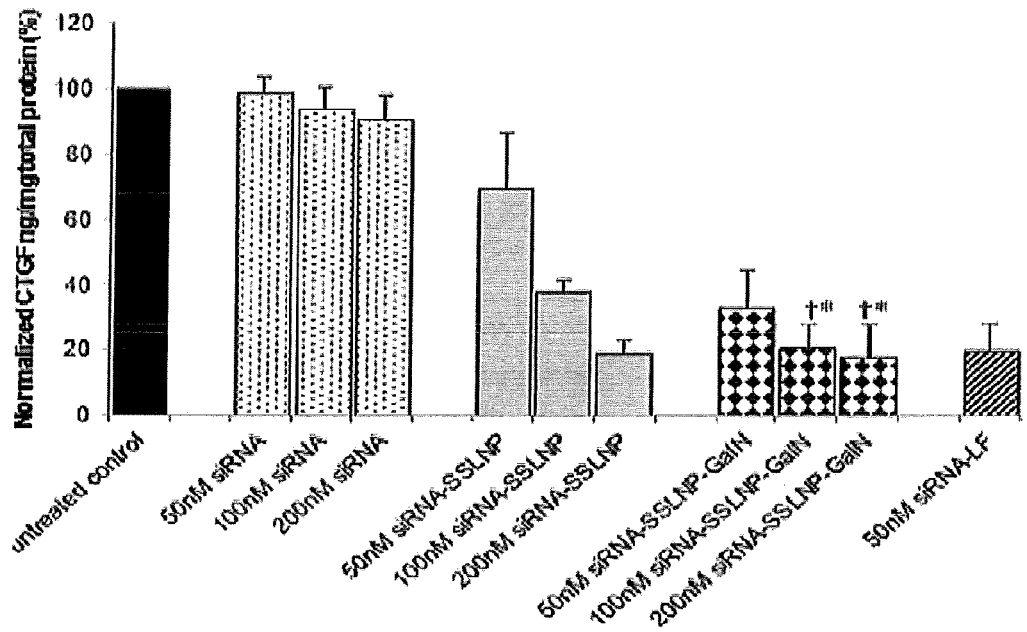
FIG. 4 shows reduced connective tissue growth factor (CTGF) expression in Hep-G2 cells transfected with siRNA in different complexes. Cells were treated with 50, 100 and 200 nM CTGF-siRNA. Reduction in protein expression was measured at 24 hours post-transfection and normalized to total protein in cells. *$p<0.05$ vs free siRNA treated cells, † $p>0.05$ vs siRNA-LIPOFECTAMINE (LF) treated cells.

Previous studies have shown that attachment of galactosamine facilitates hepatocyte targeting of a variety of uncharged polymers through asialogylcoprotein receptors (Lee, et al. (2011) *Bioorg. Med. Chem.* 19:2494-2500; Wu, et al. (2004) *Curr. Drug Deliv.* 1:119-127). As galactosamine targeting enhances endocytosis of SSLNPs, it was expected that greater gene silencing would be observed as a result of the increased amount of siRNA-SSLNP in the cells. Therefore, gene silencing potencies of different siRNA formulations were determined through the measurement of protein expression in a dose-response manner. CTGF protein was selected for analysis as it is ubiquitously expressed at high levels in Hep-G2 cells. Cells were treated with various siRNA formulations at different concentrations with siRNA-LIPOFECTAMINE as a positive control. As shown in (FIG. 4), CTGF expression was reduced by 85% in cells treated with 100 nM and 200 nM siRNA in SSLNP-GalN, a result comparable to that of LIPOFECTAMINE, while free siRNA resulted in minimum reduction in CTGF expression indicating that the gene silencing effect was due to the enhanced stability and uptake of siRNA when incorporated within SSLNPs and targeted with galactosamine.

The ability of the nanocarrier formulation to reverse the activation of myofibroblasts was also analyzed. The downmodulation of CTGF activity shifts the TGF-β/BMP-7 balance in the direction of anti-fibrosis (Gressner & Gressner (2008) Liver Int. 28:1065-1079), i.e., inhibiting ECM synthesis, Epithelial-mesenchymal transition and HSC-activation, and increasing ECM-degradation (fibrolysis). Therefore, the anti-fibrotic effect of the siRNA-SSLNP was determined by measuring the amount of collagen deposits in ECM of HSC in culture and α-SMA expression as a biomarker for HSC activation (Kisseleva, et al. (2012) Proc. Natl. Acad. Sci. USA 109:9448-9453).

Figure 5:
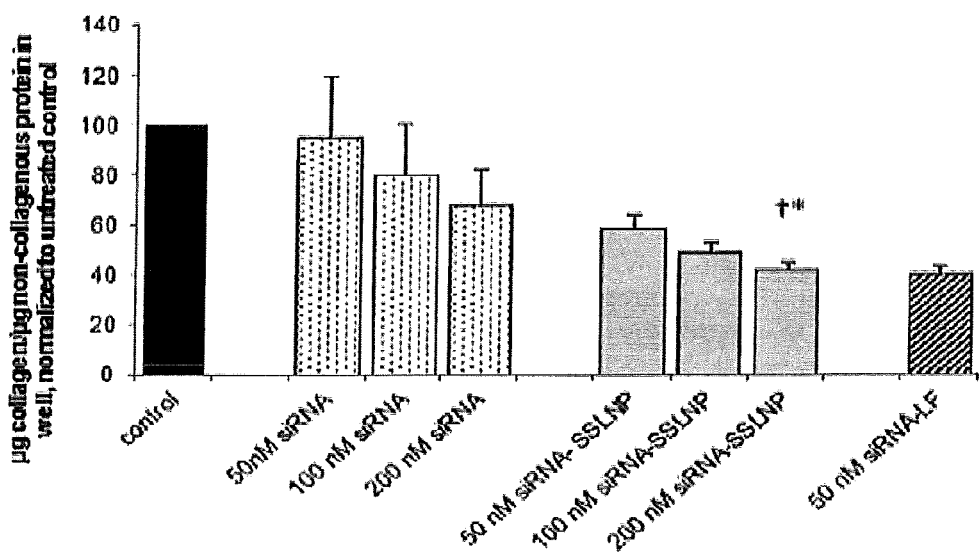
FIG. 5 shows reduced extracellular matrix collagen expression in HSC transfected with siRNA in different complexes. Cells were treated with 50, 100 and 200 nM CTGF siRNA. Reduction in protein expression was measured at 24 hours post-transfection and normalized to total non-collagenous protein in the well. *$p<0.05$ vs free siRNA treated cells, † $p>0.05$ vs siRNA-LF treated cells.

Collagen expression was measured using Sirius red/fast green kit after treatment of activated HSC with different siRNA concentrations in SSLNPs or LIPOFECTAMINE as a positive vehicle control. As shown in (FIG. 5), the reduction in collagen expression followed a dose-dependent response, with the highest reduction (52%) observed in the ECM of cells treated with 200 nM siRNA in SSLNP, a result not significantly different from that obtained with LIPOFECTAMINE. Galactosamine-targeted SSLNPs were not used in this treatment since activated myofibroblasts are not known to express asialoglycoprotein receptors. Subsequently, these results were confirmed by performing immunocytochemistry for α-SMA, Collagen type I and III of HSC cultured on glass slides. The results indicated a marked decline in the expression of these proteins in cells treated with siRNA formulated with SSLNP or LIPOFECTAMINE in comparison with free siRNA and untreated control. Collectively, these results indicate the reversal of HSC activation to an inactivated phenotype and the initiation of fibrolysis of the ECM.

Gene silencing potencies of different siRNA formulations were also determined in HK-2 cells by measuring CTGF protein expression in a dose-dependent manner. HK-2 cells were treated with various siRNA formulations at different concentrations, siRNA-LIPOFECTAMINE as a positive control, or scrambled siRNA as a negative control. CTGF concentration was determined using ELISA and calculated using generated standard curve. The results were normalized to the total protein in samples measured by Bradford protein assay This analysis indicated a 66%, 70% and 75% reduction in CTGF expression in cells treated with 50 nM, 100 nM and 200 nM siRNA in SSLNP, respectively. All three results were not significantly different from that obtained with LIPOFECTAMINE, while free siRNA resulted in a minimal reduction in CTGF expression at all the tested concentrations. No change of CTGF expression in the untreated control was observed in samples treated with scrambled siRNA. This indicates that the gene silencing effect was due to the enhanced stability and uptake of siRNA when incorporated within SSLNPs. Furthermore, the conjugation of GalN resulted in higher uptake and reduction of CTGF expression, resulting in an 80%, 82% and 86% reduction for cells treated with 50 nM, 100 nM and 200 nM siRNA, respectively.

Example 5

Reversal of HK-2 Cell Activation

Renal tubular epithelial cells undergo phenotypic activation in renal fibrosis and are responsible for the production of large amounts of ECM collagenous fibers. Thus, having demonstrated CTGF knockdown, it was determined whether the siRNA formulations had an effect on the production of ECM. siRNA in different formulations was added to the medium of TGF-β-activated HK-2 cells at increasing concentrations (50, 100 and 200 nM), wherein positive control samples were treated with LIPOFECTAMINE, and negative controls included scrambled siRNA in SSLNP-GalN. Collagen expression was measured using Sirius red/fast green kit.

This analysis indicated that the reduction in collagen expression was minimal after treatment with free siRNA, with values not exceeding 15% degradation of ECM collagen in relation to the untreated control. On the other hand, this reduction followed a dose-dependent trend in siRNA-SSLNP treated samples, showing a total collagen expression of 77%, 74% and 71% in the presence of 50 nM, 100 nM and 200 nM CTGF-siRNA respectively. However, there was no significant difference among the three doses.

Meanwhile, the galactosamine targeted formulation was found to achieve better results in terms of ECM degradation, with up to 50% reduction in total collagen, relative to that in the untreated control. This result was obtained using an siRNA concentration of 200 nM and was comparable to that achieved by LIPOFECTAMINE treatment.

Example 6

In Vivo Biodistribution (BD) and Pharmacokinetics (PK) Evaluation

The in vivo BD and PK of the nanocarrier was confirmed to demonstrate the feasibility of its use as a hepatic- and renal-targeted delivery system, as well as its role in enhancing siRNA bioavailability and pharmacokinetics parameters. Healthy male Balb/c mice were used to evaluate the behavior of the system in vivo before disease induction. Formulations were administered through tail vain, and animals were sacrificed at predetermined time points over a 24-hour period. FIGS. 6A-8F provide the content of tested formulations in different organs (FIGS. 6A-6E) as well as plasma (FIG. 6F), at various post-injection time points, as measured by Cy5 fluorescence. Significantly higher amounts of SSLNP-GalN encapsulated siRNA were detected in liver and kidneys, at any given time point, compared to free siRNA and Cy5 fluorophore (FIGS. 6A and 6E). On the other hand, the nanoparticles significantly increased the residence time of siRNA in both liver and kidneys compared to other organs (FIGS. 6A-6E), although kidney targeting was more efficient. These results indicate the advantage of using SSLNP nanocarriers for passive targeting in general and SSLNP-GalN for active hepatic and renal targeting in particular.

Pharmacokinetic parameters were calculated according to two-compartmental model analysis. Free siRNA was found to have the highest distribution half-life ($t\frac{1}{2}$, α=27.85 minutes) and plasma elimination half-life ($t\frac{1}{2}$, β=423 minutes) with the lowest volume of distribution (Vdss=0.69 ml). This could be explained by the susceptibility of highly charged siRNA to bind to protein or other plasma components resulting in the delayed tissue distribution and elimination. Meanwhile, apparent volume of distribution (Vdss) was significantly increased for siRNA encapsulated in SSLNP and SSLNP-GalN (4.51 and 3.74 ml, respectively), confirming its higher tissue uptake. The lower Vdss for the targeted nanoparticles likely results from higher accumulation of SSLNP-GalN in organs of interest (liver and kidneys), while SSLNP had higher non-specific tissue uptake. Finally, the significantly higher mean residence time (MRT) of siRNA-SSLNP (262 minutes) and siRNA-SSLNP-GalN (264 minutes) vs free siRNA (91 minutes) also demonstrates that the instant nanoparticles prolong the overall presence of siRNA in the animal body and organs of interest.

Example 7

In Vivo Efficacy

Both rat and mouse species have been widely studied as liver fibrosis animal models (Fujii, et al. (2010) *BMC Gastroenterol.* 10:79; Kim, et al. (2008) *Radiology* 247:696-705). Rats are of particular use in studying the treatment of fibrosis due to the permissible volume of blood collection and larger organs size which will allow for more accurate evaluation of disease progression through liver function test and histology studies. Liver fibrosis and cirrhosis have been induced in Sprague-Dawley rats through carbon tetrachloride ($CCl_4$) injections (Ying, et al. (2012) *J. Clin. Ultrasound.* 40(8):462-70), bile duct ligation (Oguz, et al. (2012) *Toxicol. Ind. Health* 29(9):838-45) and dimethylnitrosamine (DMN) injections (Lin, et al. (2011) J. Ethnopharmacol. 134(3):953-960), all of which are considered well-established and accepted models for liver fibrosis and cirrhosis (Sato, et al. (2008) Nat. Biotechnol. 26:431-442).

Carbon tetrachloride ($CCl_4$) are of particular use in studying fibrosis as this compound promotes the expression of CTGF protein by inducing TGF-β in hepatocytes of treated animals. In response to TGF-β, the activin receptor-like kinase (Smad3 pathway) induces the expression of CTGF. While liver fibrosis induced by bile duct ligation results in the up-regulation of PDGF increasing proliferation of activated hepatic stellate cells and expression of ECM proteins in a non-CTGF related manner (Jiao, et al. (2009) *Curr. Opin. Gastroenterol.* 25:223-229). In addition, $CCl_4$-induced hepatic fibrosis can be achieved with a less invasive procedure (IP injections over 8 weeks).

Several approaches have been reported to evaluate siRNA delivery efficiency and biodistribution in vivo using scintillation count for $^{32}P$ labeled siRNA (Gao, et al. (2009) *Mol. Ther.* 17:1225-1233), and magnetic resonance imaging (MRI) for siRNA delivered in metal-carrying nanoparticles (Ali, et al. (2009) *Mol. Pharm.* 6:1409-1416). Cy5-labeled siRNA is of particular use given its safe applicability and simple detection technique.

Liver fibrosis is induced in a group of 130 Sprague-Dawley male rats (8 weeks old) by $CCl_4$ in olive oil administered IP twice a week for 8 weeks. An additional group of 10 animals do not receive any treatment and is used as a healthy age matching control group throughout the study. The prognosis of hepatic fibrosis is evaluated through liver function tests determined from serum albumin, bilirubin, and Alanine aminotransferase (ALT) by Olympus AU400 chemistry analyzer. Fibrosis is also confirmed by histology studies performed on livers of randomly selected rats using hydroxyproline content assay and Azan-Mallory staining for collagen deposition in ECM.

A total of 100 rats is divided into 10 groups (10 animals/group) and treated with formulations summarized in Table 3 given as IV injections twice a week for two consecutive weeks.

TABLE 3

| Group | Type of Treatment |
| --- | --- |
| 0 | Healthy, untreated |
| 1 | Normal saline |
| 2 | 0.5 mg/kg free CTGF-siRNA pool |
| 3 | 1 mg/kg free CTGF-siRNA pool |
| 4 | 2 mg/kg free CTGF-siRNA pool |
| 5 | 0.5 mg/kg scrambled-siRNA in SSLNP-GalN |
| 6 | 1 mg/kg scrambled-siRNA in SSLNP-GalN |
| 7 | 2 mg/kg scrambled-siRNA in SSLNP-GalN |
| 8 | 0.5 mg/kg CTGF-siRNA pool in SSLNP-GalN |
| 9 | 1 mg/kg CTGF-siRNA pool in SSLNP-GalN |
| 10 | 2 mg/kg CTGF-siRNA pool in SSLNP-GalN |

The reversal of fibrosis is assessed by evaluating liver function tests and hydroxyproline content as well as liver morphology as mentioned above on randomly selected rats at the end of treatment.

In vivo safety of the nanocarrier is evaluated by animal survival and well-being (e.g., body weight, food intake, healthy bowel movement and complete hematology analysis) over a period of 2 months after induction of liver fibrosis. Immediate or delayed symptoms of hematological toxicity, if any, is evaluated through CBC with differentials using Advia-120 hematology analyzer at the end of two weeks of treatment and at the end of the study.

It is expected that $CCl_4$ treatment will develop fibrotic liver in rats causing alteration in liver function tests and liver histology. After treatment with siRNA-SSLNP-GalN the nanocarrier will accumulate in the liver with minimum distribution to other organs and will result in reversal of fibrosis upon multiple administrations of the formulation, which is reflected as a decrease in liver ECM collagen and restoration of liver function and histology.

What is claimed is:

1. A sterically stabilized nanocarrier comprising a PEGylated phospholipid complexed with one or more cationic phospholipids, wherein said sterically stabilized nanocarrier has a particle size of about 10 nm to about 100 nm and the cationic phospholipid has the structure of Formula I:

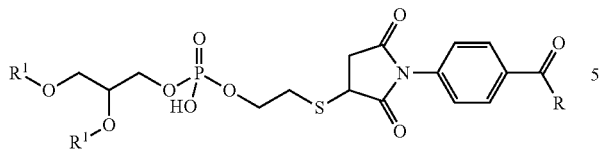

Formula I wherein R is a linear chain of between 1 and 10 basic amino acid residues and each $R^1$ is independently a saturated or unsaturated acyl chain of between 16 and 18 carbon atoms.

2. The sterically stabilized nanocarrier of claim 1, wherein the PEGylated phospholipid is distearoylglycerophosphoethanolamine-PEG$_{2000}$.

3. The sterically stabilized nanocarrier of claim 1, wherein the cationic phospholipid has the structure of Formula II:

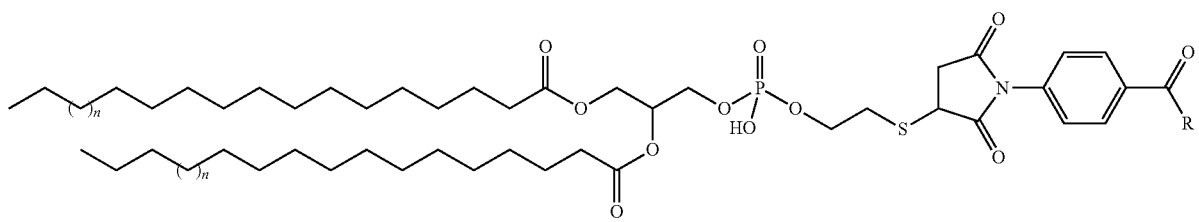

Formula II wherein each n is independently 0, 1 or 2, and R is a linear chain of between 1 and 10 arginine, lysine, or histidine residues, or a combination thereof.

4. The sterically stabilized nanocarrier of claim 3, wherein the cationic phospholipid has the structure:

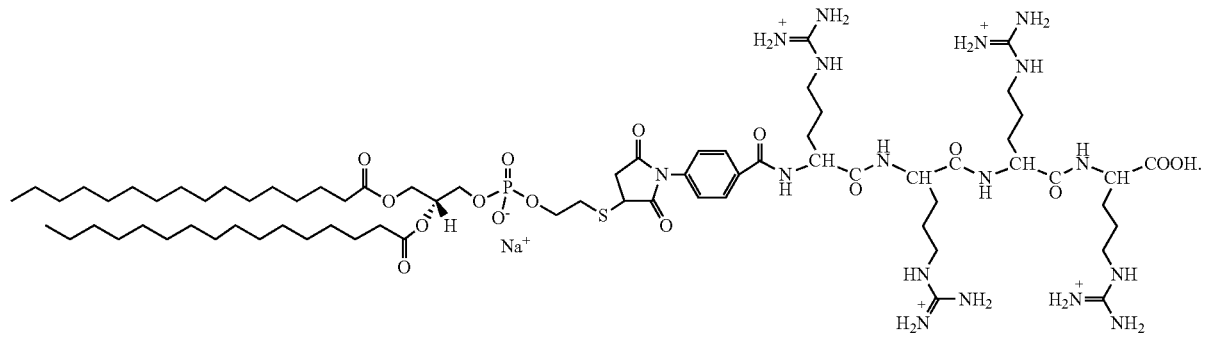

5. The sterically stabilized nanocarrier of claim 1, wherein the nanocarrier further comprises a targeting ligand.

6. The sterically stabilized nanocarrier of claim 1, wherein the nanocarrier further comprises a therapeutic agent.

7. The sterically stabilized nanocarrier of claim 5, wherein the therapeutic agent comprises an RNAi, antisense, or ribozyme molecule.

8. A compound having the structure of Formula I:

Formula I

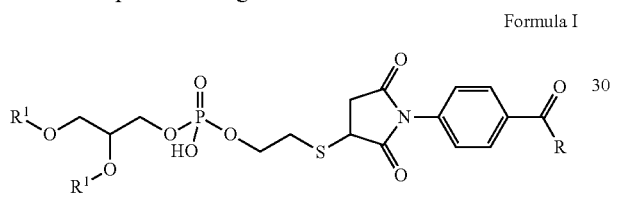

wherein R is a linear chain of between 1 and 10 basic amino acid residues and each $R^1$ is independently a saturated or unsaturated acyl chain of between 16 and 18 carbon atoms.

9. The compound of claim 8, wherein the compound has the structure of Formula II:

Formula II

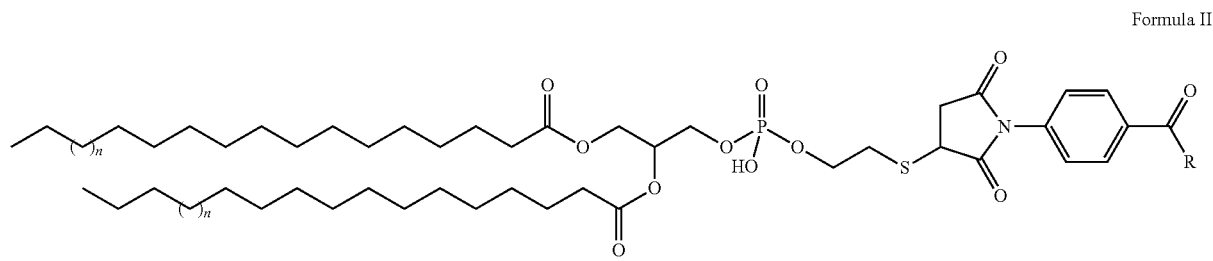

wherein each n is independently 0, 1 or 2, and R is a linear chain of between 1 and 10 arginine, lysine, or histidine residues, or a combination thereof.

10. The compound of claim 9, wherein the compound has the structure:

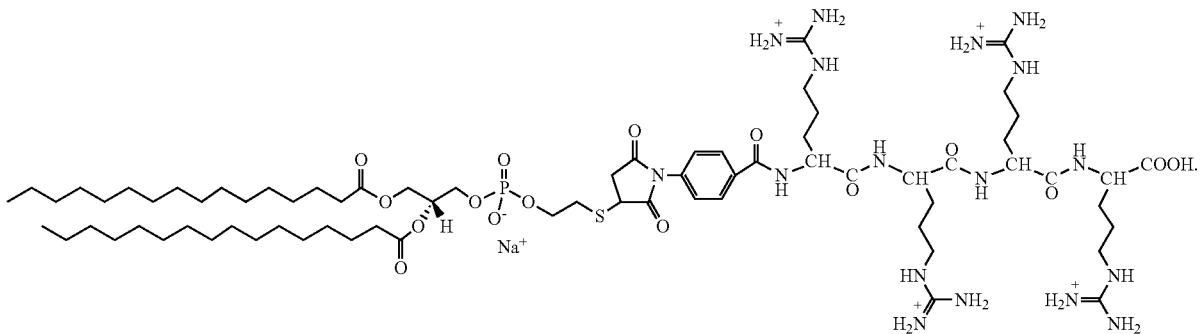

11. A sterically stabilized nanocarrier comprising the compound of claim 8.

12. The sterically stabilized nanocarrier of claim 11, wherein said nanocarrier comprises a PEGylated phospholipid.

13. The sterically stabilized nanocarrier of claim 11, wherein said nanocarrier further comprises a targeting ligand.

14. The sterically stabilized nanocarrier of claim 11, wherein said nanocarrier further comprises a therapeutic agent.

15. The sterically stabilized nanocarrier of claim 14, wherein the therapeutic agent comprises an RNAi, antisense, or ribozyme molecule.

16. A kit comprising
(a) a compound having the structure of Formula I:

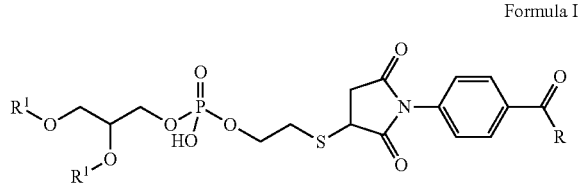

Formula I wherein R is a linear chain of between 1 and 10 basic amino acid residues and each $R^1$ is independently a saturated or unsaturated acyl chain of between 16 and 18 carbon atoms, and
(b) a PEGylated phospholipid.

17. The kit of claim 16, wherein the compound has the structure of Formula II:

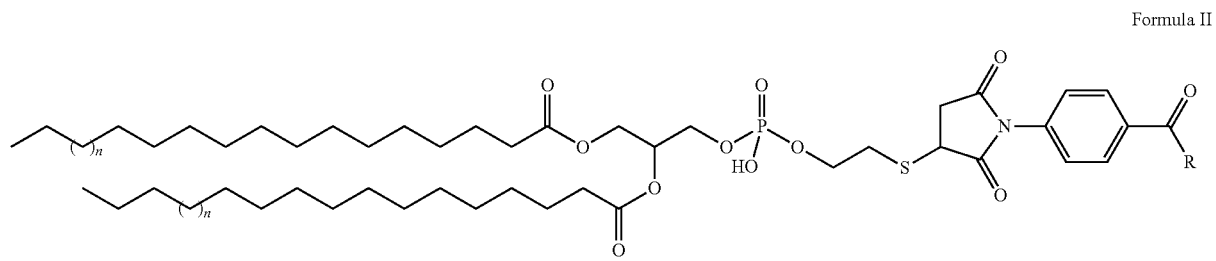

Formula II wherein each n is independently 0, 1 or 2, and R is a linear chain of between 1 and 10 arginine, lysine, or histidine residues, or a combination thereof.

18. The kit of claim 17, wherein the compound has the structure:

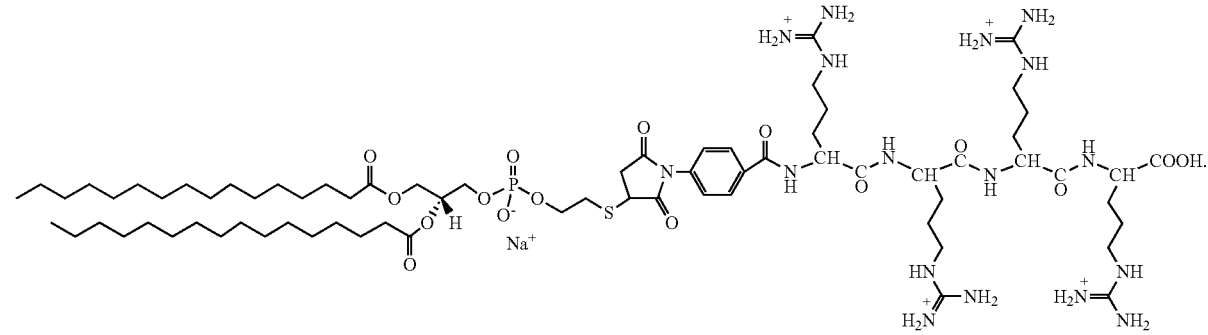

19. The kit of claim 16, further comprising a targeting ligand.

20. The kit of claim 16, further comprising a therapeutic agent.

21. The kit of claim 20, wherein the therapeutic agent comprises an RNAi, antisense, or ribozyme molecule.

22. A method for delivering a therapeutic agent to a subject comprising administering to a subject in need of treatment an effective amount of a sterically stabilized nanocarrier of claim 6 thereby delivering a therapeutic agent to the subject.

23. A method for preventing or treating a disease or condition comprising administering to a subject in need of treatment an effective amount of a sterically stabilized nanocarrier of claim 6 thereby preventing or treating the subject's disease or condition.

24. The method of claim 23, wherein the disease or condition is renal fibrosis, liver fibrosis or cirrhosis.

25. The method of claim 23, wherein the therapeutic agent is an RNAi molecule that specifically inhibits expression of connective tissue growth factor.

\* \* \* \* \*

SEQUENCE LISTING

<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Ala Thr Trp Leu Pro Pro Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Ala Pro Arg Pro Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Ser Met Ser Ile Ala Arg Leu
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide

<400> SEQUENCE: 4

Thr Ala Ala Ser Gly Val Arg Ser Met His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Leu Thr Leu Arg Trp Val Gly Leu Met Ser
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Cys Asp Ser Asp Ser Asp Ile Thr Trp Asp Gln Leu Trp Asp Leu Met
1               5                   10                  15

Lys

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Gly Pro Leu Pro Leu Arg

```
<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

His Trp Gly Phe
1

<210> SEQ ID NO 9
<211> LENGTH: 28
<212> TYPE: PRT
<213> ORGANISM: Artificial Sequence
<220> FEATURE:
<223> OTHER INFORMATION: Synthetic peptide

<400> SEQUENCE: 9

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Arg Arg Arg Arg
1
```